US012066362B2

(12) United States Patent
Matula et al.

(10) Patent No.: US 12,066,362 B2
(45) Date of Patent: Aug. 20, 2024

(54) ULTRASOUND SYSTEM FOR SHEARING CELLULAR MATERIAL

(71) Applicant: University of Washington, Seattle, WA (US)

(72) Inventors: Thomas J. Matula, Kirkland, WA (US); Karol Bomsztyk, Mercer Island, WA (US); Brian MacConaghy, Kent, WA (US); Justin Reed, Seattle, WA (US); Adam D. Maxwell, Woodinville, WA (US)

(73) Assignee: University of Washington, Seattle, WA (US)

( * ) Notice: Subject to any disclaimer, the term of this patent is extended or adjusted under 35 U.S.C. 154(b) by 294 days.

(21) Appl. No.: 17/239,387

(22) Filed: Apr. 23, 2021

(65) Prior Publication Data
US 2021/0325280 A1    Oct. 21, 2021

Related U.S. Application Data

(63) Continuation of application No. 15/326,892, filed as application No. PCT/US2015/040444 on Jul. 14, 2015, now abandoned.
(Continued)

(51) Int. Cl.
*B01L 3/00* (2006.01)
*B06B 1/02* (2006.01)
(Continued)

(52) U.S. Cl.
CPC ............ *G01N 1/286* (2013.01); *B01L 3/5085* (2013.01); *B06B 1/0215* (2013.01);
(Continued)

(58) Field of Classification Search
CPC ........................... G10K 11/30; B06B 2201/55
See application file for complete search history.

(56) References Cited

U.S. PATENT DOCUMENTS 3,949,349 A    4/1976    Massa et al.
4,874,137 A    10/1989   Chiba
(Continued)

FOREIGN PATENT DOCUMENTS

WO    WO2010118540 A1    10/2010

OTHER PUBLICATIONS

Office Action for U.S. Appl. No. 15/326,892, dated Jun. 18, 2019, Matula, "Ultrasound System for Shearing Cellular Material", 6 pages.
(Continued)

*Primary Examiner* — Natalia Levkovich
(74) *Attorney, Agent, or Firm* — Katherine M. Mead; Lee & Hayes PC

(57) ABSTRACT

A system for processing biological or other samples includes an array of transducer elements that are positioned to align with sample wells in a microplate. Each transducer element produces ultrasound energy that is focused towards a well of the microplate with sufficient acoustic pressure to cause inertial cavitation. In one embodiment, the transducers are configured to direct ultrasound energy into cylindrical wells. In other embodiments, the transducer elements are configured to direct ultrasound energy into non-cylindrical wells of a microplate.

16 Claims, 24 Drawing Sheets

Related U.S. Application Data

(60) Provisional application No. 62/025,873, filed on Jul. 17, 2014.

(51) Int. Cl.

| | |
    |---|---|
    | *B06B 1/06* | (2006.01) |
    | *C12M 1/00* | (2006.01) |
    | *G01N 1/28* | (2006.01) |
    | *G10K 11/30* | (2006.01) |

(52) U.S. Cl.
    CPC ........... *B06B 1/0629* (2013.01); *C12M 47/06* (2013.01); *G10K 11/30* (2013.01); *B06B 2201/55* (2013.01); *B06B 2201/70* (2013.01)

(56) References Cited

U.S. PATENT DOCUMENTS

| | | |
|---|---|---|
| 5,736,100 A | 4/1998 | Miyake et al. |
| 5,858,309 A | 1/1999 | Mathus et al. |
| 6,436,351 B1 | 8/2002 | Gubernator et al. |
| 6,686,195 B1 | 2/2004 | Colin et al. |
| 6,699,711 B1 | 3/2004 | Hahn et al. |
| 6,719,449 B1 | 4/2004 | Laugharn, Jr. et al. |
| 7,004,282 B2 | 2/2006 | Manna et al. |
| 7,625,746 B2 | 12/2009 | Patno et al. |
| 7,687,026 B2 | 3/2010 | Laugham, Jr. et al. |
| 7,951,337 B2 | 5/2011 | Vollert |
| 8,127,614 B2 | 3/2012 | Vivek et al. |
| 8,235,578 B2 | 8/2012 | Murakami et al. |
| 8,319,398 B2 | 11/2012 | Vivek et al. |
| 8,342,736 B2 | 1/2013 | Luotola et al. |
| 2002/0141905 A1 | 10/2002 | Sha et al. |
| 2005/0106074 A1 | 5/2005 | Sakamoto |
| 2009/0233814 A1 | 9/2009 | Bashkirov et al. |
| 2009/0254289 A1* | 10/2009 | Vivek .................. B06B 1/0622 702/54 |
| 2010/0028988 A1 | 2/2010 | Chu et al. |
| 2010/0289887 A1 | 11/2010 | Charlot et al. |
| 2013/0010567 A1 | 1/2013 | Nikolovski et al. |

OTHER PUBLICATIONS

Oeffinger M, Wei KE, Rogers R, DeGrasse JA, Chait BT, et al. (2007) Comprehensive analysis of diverse ribonucleoprotein complexes. Nat Methods 4: 951-956.

Orlando V, Strutt H, Paro R (1997) Analysis of chromatin structure by in vivo formaldehyde cross-linking. Methods 11: 205-214.

Ostareck DH, Ostareck-Lederer A, Wilm M, Thiele BJ, Mann M, et al. (1997) mRNA silencing in erythroid differentiation: hnRNP K nad hnRNP E1 regulate 15-lipogenase translation from the 3' end. Cell 89: 597-606.

Ostrowski J, Bomsztyk K (2000) Increased K protein expression in serum-treated hepatocytes, posthepactomized livers and liver tumors. (manuscript in preparetion).

Ostrowski J, Woszczynski M, Kowalczyk P, Wocial T, Hennig, E.,, Trzeciak L, et al. (2000) Increased activity of MAP, p70S6 and p90rs kinases is associated with AP-1 activation in spontenous liver tumors, but no in adjacent tissue in mice. BriJCancer 82: 1041-1050.

Ostrowski J, Bomsztyk K (2003) Nuclear shift of hnRNP K protein in neoplasm and other states of enhanced cell proliferation. Br J Cancer 89: 1493-1501.

International Search Report dated Oct. 15, 2015 in International Patent Application No. PCT/US2015/040444, 12 pages.

Pokholok DK, Zeitlinger J, Hannett NM, Reynolds DB, Young RA (2006) Activated signal transduction kinases frequently occupy target genes. Science 313: 533-536.

Rothberg JM, Hinz W, Rearick TM, Schultz J, Mileski W, et al. (2011) An integrated semiconductor device enabling non-optical genome sequencing. Nature 475: 348-352.

Sanduja S, Blanco FF, Dixon DA (2010) The roles of TTP and BRF proteins in regulated mRNA decay. WIREs RNA 2: 42-57.

Shen Z, St-Denis A, Chartrand P (2010) Cotranscriptional recruitment of She2p by RNA pol II elongation factor Spt4-Spt5/DSIF promotes mRNA localization to the yeast bud. Genes Dev 24:1914-1926.

Sims RJ, 3rd, Mandal SS, Reinberg D (2004) Recent highlights of RNA-polymerase-II-mediated transcription. Curr Opin Cell Biol 16: 263-271.

Siomi H, Dreyfuss G (1995) A nuclear localization domain in the hnRNP A1 protein. JCellBiol 129: 551-560.

Solomon MJ, Varshavsky A (1985) Formaldehyde-mediated DNA-protein crosslinking: a probe for in vivo chromatin structures. Proc Natl Acad Sci U S A 82: 6470-6474.

Solomon MJ, Larsen PL, Varshavsky A (1988) Mapping protein-DNA interactions in vivo with formaldehyde: evidence that histone H4 is retained on a highly transcribed gene. Cell 53: 937-947.

Sorensen AL, Collas P (2009) Immunoprecipitation of methylated DNA. Methods Mol Biol 567: 249-262.

Swinburne IA, Meyer CA, Liu XS, Silver PA, Brodsky AS (2006) Genomic localization of RNA binding proteins reveals links between pre-mRNA processing and transcription. Genome Res 16: 912-921.

Tandiono, Ohl SW, Ow DS, Klaseboer E, Wong VV, et al. (2010) Creation of cavitation activity in a microfluidic device through acoustically driven capillary waves. Lab Chip 10: 1848-1855.

Tavakkoli J, Cathignol D, Souchon R, Sapozhnikov OA (1998) Modeling of pulsed finite-amplitude focused sound beams in time domain. J Acoust Soc Am 104: 2061-2072.

Thiriet C, Hayes JJ (2005) Chromatin in need of a fix: phosphorylation of H2AX connects chromatin to DNA repair. Mol Cell 18: 617-622.

Toth J, Biggin MD (2000) The specificity of protein-DNA crosslinking by formaldehyde: in vitro and in *Drosophila* embryos. Nucleic Acids Res 28: e4.

Ule J, Jensen KB, Ruggiu M, Mele A, Ule A, et al. (2003) CLIP identifies Nova-regulated RNA networks in the brain. Science 302: 1212-1215.

Ule J, Jensen K, Mele A, Darnell RB (2005) CLIP: a method for identifying protein-RNA interaction sites in living cells. Methods 37: 376-386.

Van der Houven van Oordt W, Diaz-Meco MT, Lozano J, Krainer AR, Moscat J, et al. (2000) The MKK(3/6)-p38-signaling cascade alters the subcellular distribution of hnRNP A1 and modulates alternative splicing regulation. J Cell Biol 149: 307-316.

Wu AR, Hiatt JB, Lu R, Attema JL, Lobo NA, et al. (2009) Automated microfluidic chromatin immunoprecipitation from 2,000 cells. Lab Chip 9: 1365-1370.

Yu J, Feng Q, Ruan Y, Komers R, Kiviat N, et al. (2011) Microplate-based platform for combined chromatin and DNA methylation immunoprecipitation assays. BMC Mol Biol 12: 49.

Aker M, Bomsztyk K, Emery DW (2010) Poly(Adp-Ribose) polymerase-1 (Parp-1) contributes to the barrier function of a vertebrate chromatin insulator. J Biol Chem 285: 37589-37597.

Bekenstein U, Soreq H (2012) Heterogeneous nuclear ribonucleoprotein A1 in health and neurodegenerative disease: From structural insights to post-transcriptional regulatory roles. Mol Cell Neurosci.

Brodsky AS, Meyer CA, Swinburne IA, Hall G, Keenan BJ, et al. (2005) Genomic mapping of RNA polymerase II reveals sites of co-transcriptional regulation in human cells. Genome Biol 6: R64.

Bungard D, Fuerth BJ, Zeng PY, Faubert B, Mass NL, et al. (2010) Signaling Kinase AMPK Activates Stress-Promoted Transcription via Histone H2B Phosphorylation. Science 329: 1201-1205.

Burd CG, Dreyfuss G (1994) RNA binding specificity of hnRNP A1: significance of hnRNP A1 high-affinity binding sites in pre-mRNA splicing. Embo J 13: 1197-1204.

Chooi WY (1980) Purification of *Drosophila ribosomal* proteins. Isolation of proteins S8, S13, S14, S16, S19, S20/L24, S22/L26, S24, S25/S27, S26, S29, L4, L10/L11, L12, L13, L16, L18, L19, L27, 1, 7/8, 9, and 11. Biochemistry 19: 3469-3476.

Dahl JA, Collas P (2008) A rapid micro chromatin immunoprecipitation assay (microChIP). Nat Protoc 3: 1032-1045.

Examination Report dated Apr. 26, 2018 in European Patent Application No. 15822755.3, 4 pages.

(56) References Cited

OTHER PUBLICATIONS

Extended European Search Report dated Jun. 29, 2017 in European Patent Application No. 15822755.3, 9 pages.
Supplementary European Search Report dated Jul. 18, 2017 in European Patent Application No. 15822755.3, 1 page.
Evans JR, Mitchell SA, Spriggs KA, Ostrowski J, Bomsztyk K, et al. (2003) Members of the poly (rC) binding protein family stimulate the activity of the c-myc internal ribosome entry segment in vitro and in vivo. Oncogene 22: 8012-8020.
Fanelli M, Amatori S, Barozzi I, Soncini M, Dal Zuffo R, et al. (2010) Pathology tissue-chromatin immunoprecipitation, coupled with high-throughput sequencing, allows the epigenetic profiling of patient samples. Proc Natl Acad Sci U S A.
Felsenfeld G, Groudine M (2003) Controlling the double helix. Nature 421: 448-453.
Flanagin S, Nelson JD, Castner DG, Denisenko O, Bomsztyk K (2008) Microplate-based chromatin immunoprecipitation method, Matrix ChIP: a platform to study signaling of complex genomic events. Nucleic Acids Res 36: e17.
Garber M, Yosef N, Goren A, Raychowdhury R, Thielke A, et al. (2012) A high-throughput chromatin immunoprecipitation approach reveals principles of dynamic gene regulation in mammals. Mol Cell 47: 810-822.
Glisovic T, Bachorik JL, Yong J, Dreyfuss G (2008) RNA-binding proteins and posttranscriptional gene regulation. FEBS Lett 582: 1977-1986.
Hocine S, Singer RH, Grunwald D (2010) RNA processing and export. Cold Spring Harb Perspect Biol 2: a000752.
Impey S, McCorkle SR, Cha-Molstad H, Dwyer JM, Yochum GS, et al. (2004) Defining the CREB regulon: a genome-wide analysis of transcription factor regulatory regions. Cell 119:1041-1054.
Keene JD, Komisarow JM, Friedersdorf MB (2006) RIP-Chip: the isolation and identification of mRNAs, microRNAs and protein components of ribonucleoprotein complexes from cell extracts. Nat Protoc 1: 302-307.
Keene JD (2007) RNA regulons: coordination of post-transcriptional events. Nat Rev Genet 8:533-543.
Keene JD (2010) The global dynamics of RNA stability orchestrates responses to cellular activation. BMC Biol 8: 95.
Kino G (1987) Acoustic Waves: Devices, Imaging, and Analog Signal Processing 1987. New Jersey: Prentice Hall.
Kishore S, Jaskiewicz L, Burger L, Hausser J, Khorshid M, et al. (2011) A quantitative analysis of CLIP methods for identifying binding sites of RNA-binding proteins. Nat Methods 8: 559-564.
Klimek-Tomczak K, Mikula M, Dzwonek A, Paziewska A, Karczmarski J, et al. (2006) Editing of hnRNP K protein mRNA in colorectal adenocarcinoma and surrounding mucosa. Br J Cancer 94: 586-592.
Kuo MH, Allis CD (1999) In vivo cross-linking and immunoprecipitation for studying dynamic Protein:DNA associations in a chromatin environment. Methods 19: 425-433.
Lau JS, Baumeister P, Kim E, Roy B, Hsieh TY, et al. (2000) Heterogeneous nuclear ribonucleoproteins as regulators of gene expression through interactions with the human thymidine kinase promoter [In Process Citation]. J Cell Biochem 79: 395-406.
Lefevre P, Bonifer C (2006) Analyzing histone modification using crosslinked chromatin treated with micrococcal nuclease. Methods Mol Biol 325: 315-325.
Listerman I, Sapra AK, Neugebauer KM (2006) Cotranscriptional coupling of splicing factor recruitment and precursor messenger RNA splicing in mammalian cells. Nat Struct Mol Biol.
Matula TJ, Hilmo PR, Bailey MR (2005) A suppressor to prevent direct wave-induced cavitation in shock wave therapy devices. Journal of the Acoustical Society of America 118: 178-185.
Matula TJ (1999) Inertial cavitation and single-bubble sonoluminescence. Philosophical Transactions of the Royal Society a—Mathematical Physical and Engineering Sciences 357: 225-249.
Medeiros RB, Papenfuss KJ, Hoium B, Coley K, Jadrich J, et al. (2009) Novel sequential ChIP and simplified basic ChIP protocols for promoter co-occupancy and target gene identification in human embryonic stem cells. BMC Biotechnol 9: 59.
Meissner A, Mikkelsen TS, Gu H, Wernig M, Hanna J, et al. (2008) Genome-scale DNA methylation maps of pluripotent and differentiated cells. Nature 454: 766-770.
Mikula M, Bomsztyk K (2011) Direct recruitment of ERK cascade components to inducible genes is regulated by the heterogeneous nuclear ribonucleoprotein (HnRNP) K. J Biol Chem 286: 9763-9775.
Mikula M, Hanusek K, Paziewska A, Dzwonek A, Rubel T, et al. (2010) Halogenated imidazole derivatives block RNA polymerase II elongation along mitogen inducible genes. BMC Mol Biol 11: 4.
Mikula M, Goryca, K., Bomsztyk, K., and Ostrowski, J. (2013) HnRNPK protein genome wide binding survey reveals its role in regulating 3' end RNA processing and transcription termination at EGR1 gene through XRN2 exonuclease. (in revision).
Mikula M, Dzwonek A, Karczmarski J, Rubel T, Dadlez M, et al. (2006) Landscape of the hnRNP K protein-protein interactome. Proteomics 6: 2395-2406.
Mili S, Shu HJ, Zhao Y, Pinol-Roma S (2001) Distinct RNP complexes of shuttling hnRNP proteins with pre-mRNA and mRNA: candidate intermediates in formation and export of mRNA. Mol Cell Biol 21: 7307-7319.
Moore MJ (2005) From birth to death: the complex lives of eukaryotic mRNAs. Science 309: 1514-1518.
Naito M, Zager RA, Bomsztyk K (2009) BRG1 increases transcription of proinflammatory genes in renal ischemia. J Am Soc Nephrol 20: 1787-1796.
Nelson JD, Leboeuf RC, Bomsztyk K (2011) Direct recruitment of insulin receptor and ERK signaling cascade to insulin-inducible gene loci. Diabetes 60: 127-137.
Nelson JD, Denisenko O, Sova P, Bomsztyk K (2006) Fast chromatin immunoprecipitation assay. Nucleic Acids Res 34: e2.
Nelson J, Denisenko O, Bomsztyk K (2011) Profiling RNA polymerase II using the fast chromatin immunoprecipitation method. Methods Mol Biol 703: 219-234.
Nelson JD, Denisenko O, Bomsztyk K (2006) Protocol for the fast chromatin immunoprecipitation (ChIP) method. Nat Protoc 1: 179-185.
Niranjanakumari S, Lasda E, Brazas R, Garcia-Blanco MA (2002) Reversible cross-linking combined with immunoprecipitation to study RNA-protein interactions in vivo. Methods 26: 182-190.
Notari M, Neviani P, Santhanam R, Blaser BW, Chang JS, et al. (2006) A MAPK/HNRPK pathway controls BCR/ABL oncogenic potential by regulating MYC mRNA translation. Blood 107: 2507-2516.
Office Action for U.S. Appl. No. 15/326,892, dated Jan. 25, 2021, Matula, "Ultrasound System for Shearing Cellular Material", 8 pages.
Office Action for U.S. Appl. No. 15/326,892, dated Oct. 8, 2019, Matula, "Ultrasound System for Shearing Cellular Material", 8 pages.
Office Action for U.S. Appl. No. 15/326,892, dated Oct. 8, 2020, Matula, "Ultrasound System for Shearing Cellular Material", 6 pages.
Office Action for U.S. Appl. No. 15/326,892, dated Apr. 6, 2020, Matula, "Ultrasound System for Shearing Cellular Material", 9 pages.
Acord J, Maskell J, Sefton A (2005) A rapid microplate method for quantifying inhibition of bacterial adhesion to eukaryotic cells. J Microbiol Methods 60: 55-62.

\* cited by examiner

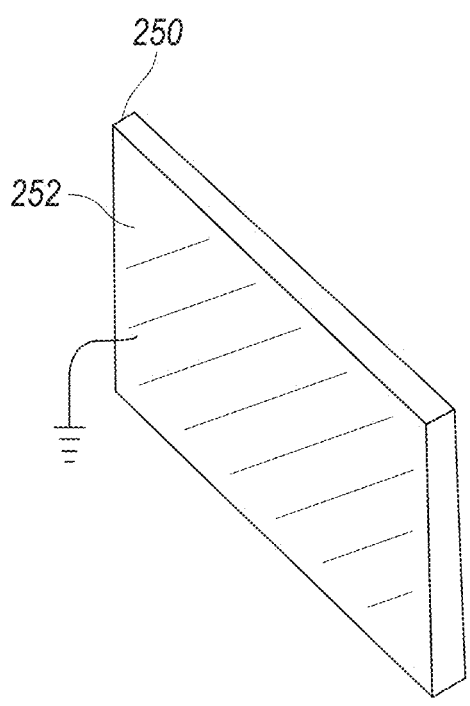
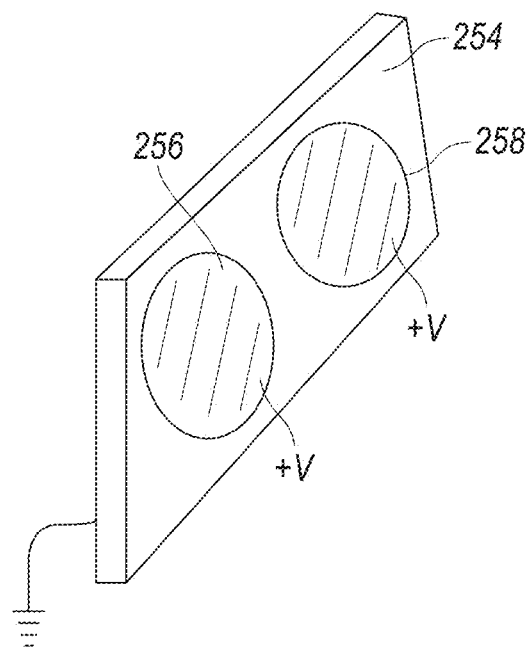
Fig. 6A
Fig. 6B

ULTRASOUND SYSTEM FOR SHEARING CELLULAR MATERIAL

CROSS-REFERENCE TO RELATED APPLICATIONS

This application is a continuation of U.S. patent application Ser. No. 15/326,892, filed Jan. 17, 2017, which is a U.S. national phase of International Patent Application No. PCT/US2015/040444, filed Jul. 14, 2015, which is related to, and claims the benefit of, U.S. Provisional Patent Application No. 62/025,873 filed Jul. 17, 2014, all of which are incorporated herein by reference in their entirety.

STATEMENT REGARDING FEDERALLY SPONSORED RESEARCH

This invention was made with government support under grant nos. 1 R21 GM 111439-01 and 1 R33 CA 191135-01 awarded by the National Institutes of Health. The government has certain rights in the invention.

TECHNICAL FIELD

The disclosed technology relates to systems for preparing materials for analysis and in particular to systems for shearing cellular material by cavitation.

BACKGROUND

Sample preparation is one of the preliminary steps that is performed before biological samples are analyzed. Sample preparation often involves the breakdown of the material into cellular or subcellular fragments. One particular application is the breaking up (or shearing) of DNA or Chromatin into smaller fragments. Ultrasound is one known method of breaking down material. In some prior art devices, biological samples are placed into a test tube that is put into a liquid bath and subjected to high intensity ultrasound waves—similar to a jewelry cleaner, but with much high power. To avoid an uneven exposure of the sample, the test tube is moved around within the ultrasound field as it is processed. While this approach does work, it is limited to processing a single test tube sample at a time.

To increase the throughput of cellular processing, some systems have proposed analyzing cellular samples in microplates. As will be appreciated by those skilled in the art, a microplate is a tray that contains an array of wells in which samples can be placed for analysis. Advantages of using microplates include the fact that such trays are easily processed with automated equipment and that multiple samples can be processed at the same time without moving the samples from one vessel to another. One system for shearing cellular samples in a microplate uses ultrasonically vibrating pins that extend into the wells. However, this can lead to cross contamination between the various wells and requires extensive cleaning of the pins. It is also not very useful for tissue samples. Furthermore, the quality of the results depends greatly on the exact position of the tips in the sample. Another approach uses a large ultrasound transducer that is positioned below a single well and focuses the energy within the well. The focused ultrasound energy creates cavitation in the sample material that is in the well but only one well is processed at a time. For a 96 element microplate, the processing time to shear all the samples can exceed several hours during which some samples may degrade.

Another suggested approach to processing cellular material in a microplate is to place a single ultrasound transducer below each well. See for example U.S. Pat. No. 6,699,711 to Hahn et al. ("Hahn"). However, when trying to experiment with the system described in the Hahn patent for use in analyzing biological materials including DNA and chromatin, it was found that the system was ineffective in shearing chromatin without causing the transducers to break.

Given these problems, there is a need for a system that can both process cellular samples in parallel using high (negative) acoustic pressures to induce or facilitate shearing, and can be operated in a manner that doesn't destroy the transducers.

BRIEF SUMMARY

The disclosed technology relates to systems for applying ultrasound to a number of samples that simultaneously induces and/or enhances cavitation in the samples. As will be described in further detail below, the disclosed technology uses transducer elements that are configured such that the stresses generated while the transducer is producing ultrasonic energy are not concentrated at a normal vibrational mode of the transducer element itself. In one embodiment, two or more transducers are formed on a sheet of piezoelectric material to form an array. In another embodiment, an array of transducer elements is created by securing individual transducers to a common support that absorbs the stresses created by the individual transducer elements.

In one embodiment, an array of two or more transducers is formed from a single sheet of piezoelectric substrate material. In one embodiment, a lens is positioned in front of each transducer and focuses the ultrasound produced by the transducers towards a well of a microplate. The transducers are driven to a level that induces inertial cavitation in a biological sample that is in the well. Multiple transducers are driven in parallel to simultaneously process the material in the wells of the microplate. In another embodiment, the transducers are curved to focus the acoustic energy so that a separate lens is not needed.

In one embodiment, an array of transducer elements is formed from a sheet of piezoelectric material having one side with a conductive material disposed on the majority of the surface and a second side with a conductive material that is patterned into two or more transducer elements that are not electrically connected and have a shape that corresponds substantially to the shape of the wells in the microplate. Electrical connections are made to supply a varying voltage across the transducer elements. A microplate having flat well bottoms is placed over the transducers. A lens is positioned between each transducer element and a well of a microplate to focus ultrasound generated by each transducer towards the corresponding well.

In another embodiment of the disclosed technology, the wells of the microplate are conical in shape. For this style of microplate, the transducer elements are shaped to surround a portion of the wells. The acoustic energy passes into the well from the sides, not from the bottom. The transducer elements may be generally spherical, hemispherical, cylindrical or annular with a center region that receives a portion of a conical well of a microplate.

In one embodiment, a plate containing a separate lens for each transducer element is positioned between the transducer element and a microplate well. In another embodiment, a lens is built into each microplate well itself, which operates to focus ultrasound towards an interior portion of the well.

BRIEF DESCRIPTION OF THE DRAWINGS

FIGS. 6A and 6B show one embodiment of an array of transducers for use in a transducer assembly in accordance with an embodiment of the disclosed technology;

DETAILED DESCRIPTION

As will be discussed in further detail below, the disclosed technology relates to a system for applying a sufficient amount of ultrasound energy to a number of samples in order to cause some shearing of the molecular bonds in the samples. In one embodiment, the system simultaneously subjects a number of samples that are in the wells of a microplate to a sufficient level of ultrasound energy that causes inertial cavitation to occur in the samples.

Figure 1:
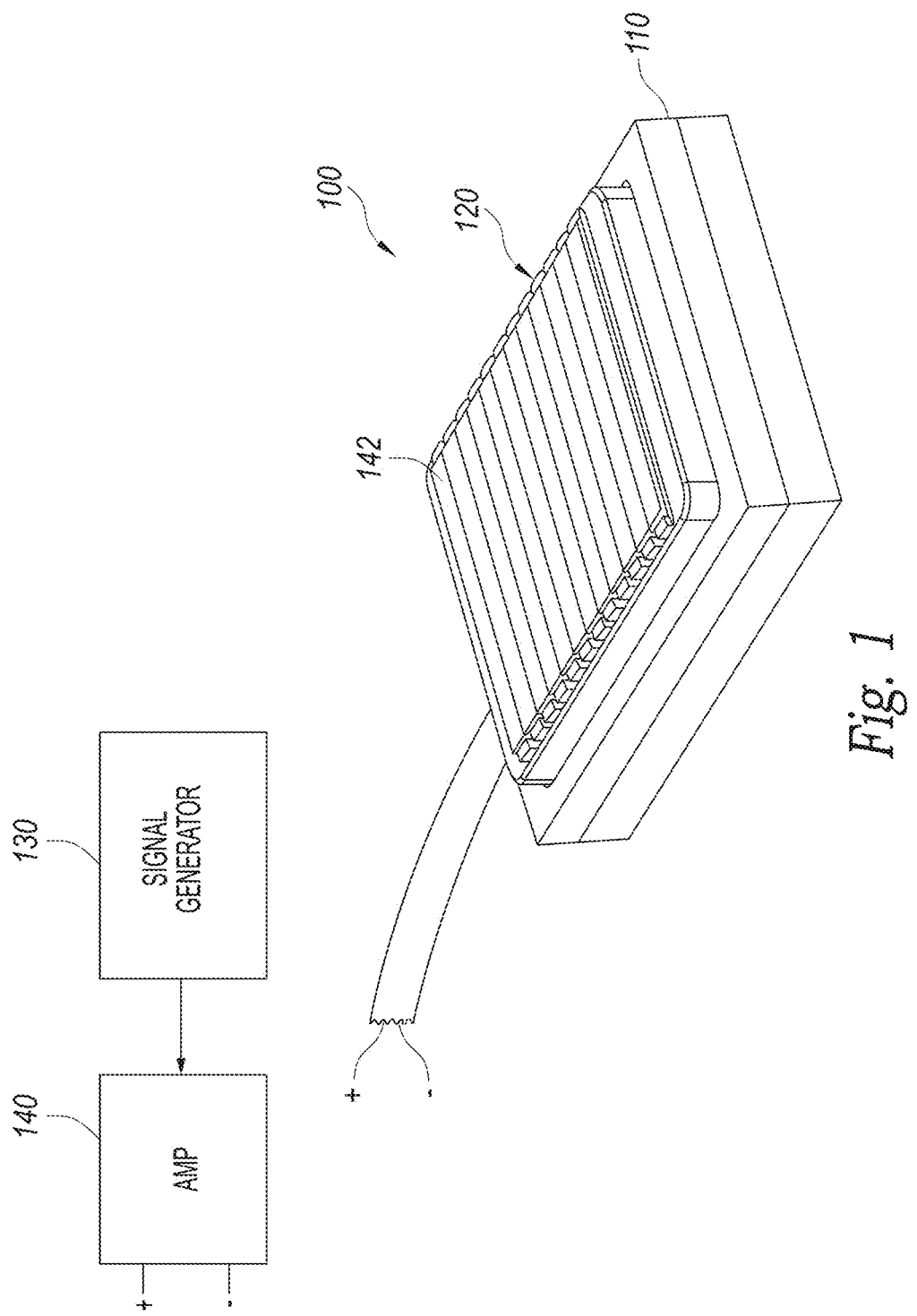
FIG. 1 is a diagram of an ultrasound shearing system in accordance with one embodiment of the disclosed technology.

As shown in FIG. 1, a system 100 includes a transducer assembly 110 that receives a microplate 120 having a number of sample wells (not individually shown) that contains samples of biological or other materials. A signal generator 130 provides a driving signal that is applied to an amplifier 140 that in turn increases the power of the signals and supplies the amplified signals to the transducer assembly 110. Individual transducers in the transducer assembly convert the amplified driving signals into acoustic energy that is sufficient to shear the materials into components. In one embodiment, the acoustic energy is simultaneously applied to each well of the microplate, and the processing time for the samples is reduced. Furthermore, the samples may remain in the individual wells of the microplate and therefore may not need to be moved to another container for further processing. In the embodiment shown, a spill cover 142 is placed over the individual wells of the microplate 120 to prevent cross contamination of the wells of the microplate. The spill cover may or may not have fingers (not shown) that protrude into the samples when the cover is in place and can be temperature controlled by, for example, running a cooling liquid through passageways (not shown) in a top cover.

Figure 2:
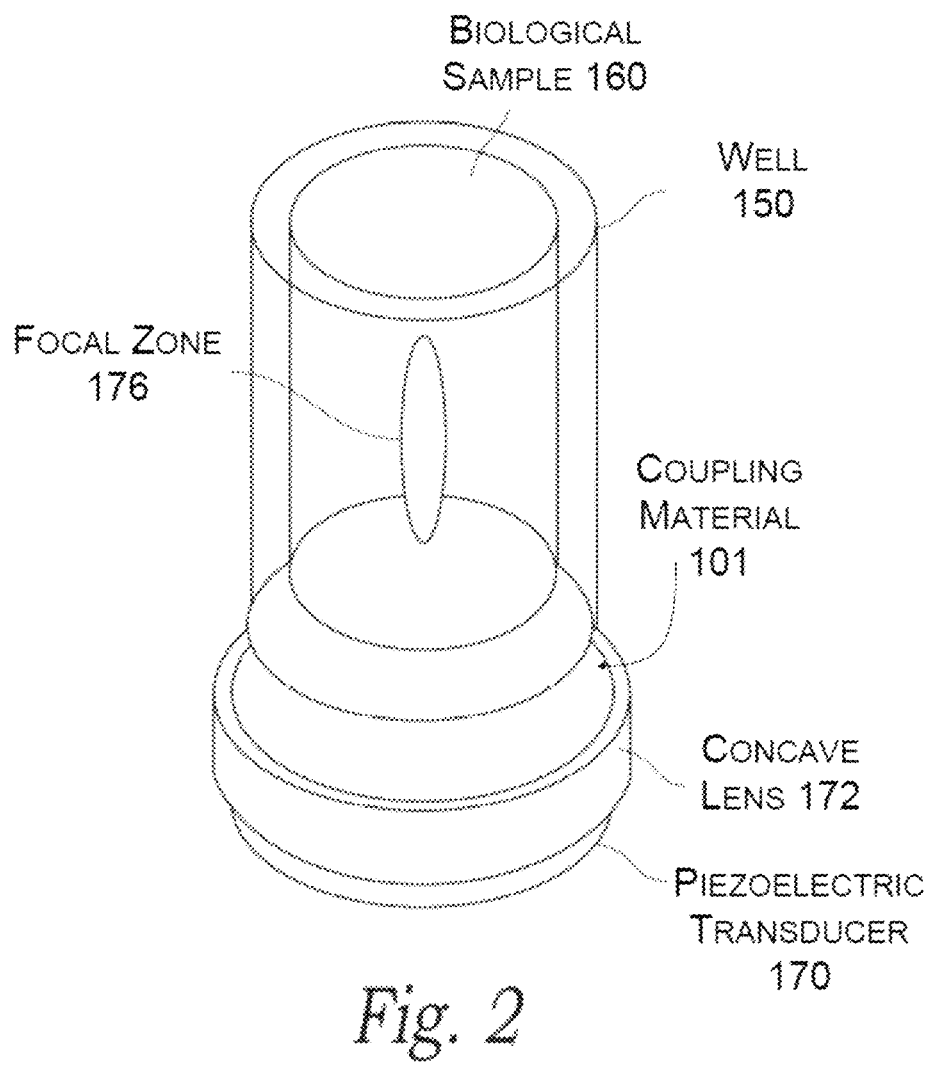
FIG. 2 illustrates a simulated focal zone created in a well of a microplate in accordance with an embodiment of the disclosed technology.

FIG. 2 is a simulation of the ultrasound energy that is created by a transducer in a single well of a microplate. In this example, a single cylindrical well 150 is part of a larger microplate (not shown) and contains a biological sample 160 in the well. A piezoelectric transducer 170 is positioned below the well 150 and produces ultrasonic energy. The energy is focused by a concave lens 172 that is positioned between the transducer 170 and the bottom of the well 150. Typically there would also be some coupling fluid such as water or a gel (not shown) that is located between the lens 172 and the bottom of the well 150 in order to provide a good acoustic coupling and to reduce reflections. The lens focuses the acoustic energy into a focal zone 176 that is towards the well 150 at pressure levels that are sufficient to cause inertial cavitation in the sample 160. Inertial cavitation causes bubbles to be created in the sample that collapse with an energy that is sufficient to shear the biological material into smaller components. In one embodiment, the focused acoustic energy is sufficient to cause chromatin shearing to yield 100-300 base pair fragments in each well of the microplate (e.g. an acoustic pressure amplitude of >1 Megapascal). This figure is representative only and does not consider the complications of having a mixture of bubbles in the sample, nor having a finite volume of liquid in the well. It will be appreciated that the focus of the transducer element need not necessarily be in the well itself. Cavitation can still occur in a sample that is located in a pre-focal or post-focal area. Therefore, the lens need only focus the ultrasound towards the well and not necessarily into the well itself.

Figure 3:
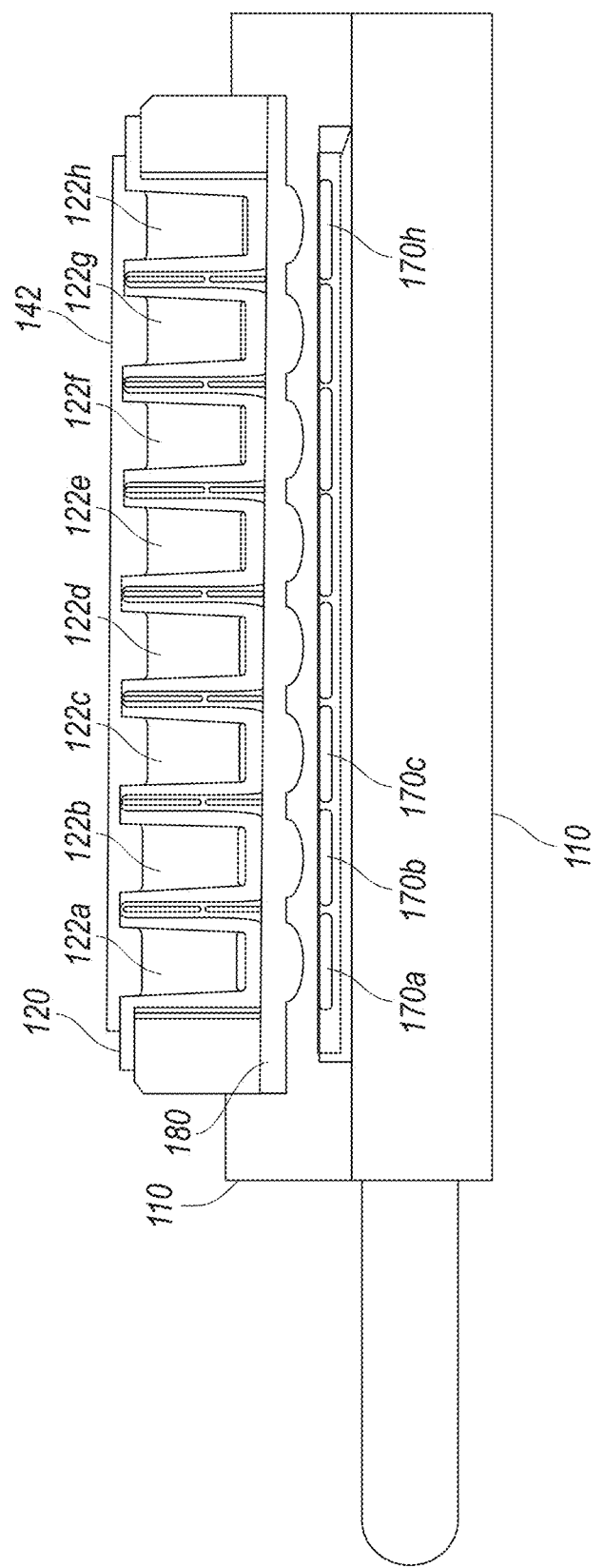
FIG. 3 illustrates a cross section of a transducer assembly showing a relationship between a number of microplate wells and a corresponding number of ultrasound transducers in accordance with an embodiment of the disclosed technology.

FIG. 3 illustrates a cross-sectional view of one possible embodiment of the ultrasound transducer assembly 110 and the microplate 120. The microplate 120 includes a number of individual generally cylindrical wells 122a, 122b, 122c . . . 122h. In one embodiment, the microplate 120 has 96 individual wells arranged in an 8×12 grid. However, it will be appreciated that other sizes of microplates could be used, and the transducer array could be adjusted to fit the appropriate microplate well configuration (number of elements and size of each element).

Positioned below each individual well of the microplate is one or more corresponding ultrasound transducers. For example, an ultrasound transducer 170a is positioned below well 122a. An ultrasound transducer 170b is positioned below well 122b etc. A coupling material 180 such as degassed water or a gel is positioned between the ultrasound transducers and the individual wells to provide a good acoustic coupling for the acoustic energy produced by the ultrasound transducers into the material contained in each of the wells.

In some embodiments, the transducer assembly 110 can include a locking top cover that is placed over the wells of the microplate hold the microplate in relation to the transducers.

Figure 4:
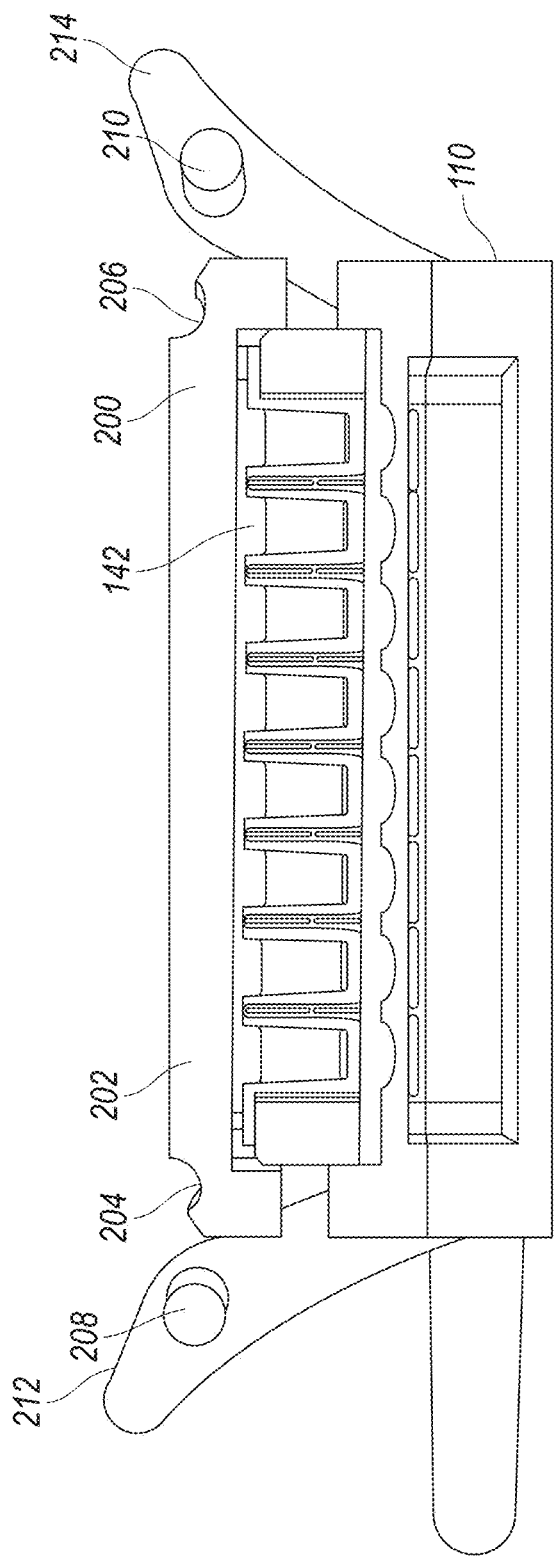
FIG. 4 shows an embodiment of the transducer assembly with a cover in an unlocked position.
Figure 5:
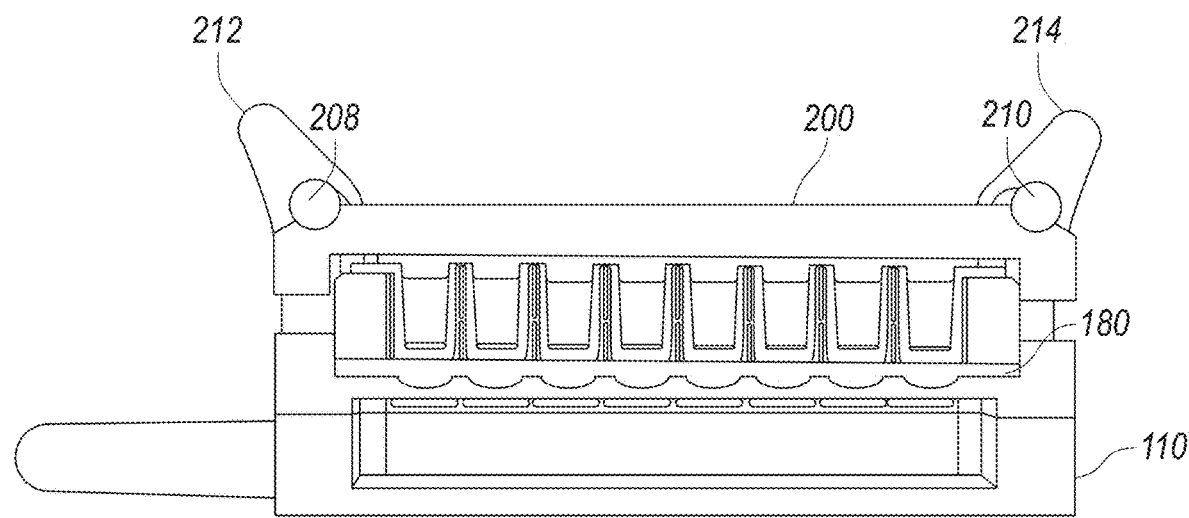
FIG. 5 shows the transducer assembly of FIG. 4 with the cover in a locked position.

FIG. 4 shows a top cover 200 having an inner surface 202 that is sized to fit over the outer perimeter of the microplate 120 and over the spill cover 142. The top surface of the top cover 200 includes first and second cylindrical detents 204, 206 on opposite sides thereof. The detents 204 and 206 are shaped to receive corresponding cylindrical rods 208 and 210 that are located on arms 212 and 214 that are hinged to the transducer assembly 110. When the hinged arms are positioned in the unlocked position, the rods 208 and 210 swing away from the detents 204, 206 on the top of the cover and the cover can be lifted off the microplate. When the arms are rotated to a locked position, the rod 208 engages the detent 204 and the rod 210 engages the detent 206 as shown in FIG. 5. With the arms in the locked position, the top cover 200 is secured over the micro plate and to the ultrasound transducer assembly 110 as shown in FIG. 5. This is one possible embodiment for a cover, and it is recognized that many other ways to hold the microplate in place can be used. The top cover can also be kept cool to help reduce sample heating by running coolant through slots in the top cover, or by directly cooling the cover itself. In one embodiment, the coupling material 180 that is positioned between the wells of the microplate and the individual transducer elements remains static. In another embodiment, the coupling material can be kept moving through ports (not shown) on the transducer assembly with a pump mechanism or the like in order to remove heat that is created during the application of ultrasound energy to the individual wells.

One of the problems encountered in applying ultrasound energy to the wells with an acoustic pressure that is sufficient to create shearing in a sample is that the transducers can crack or be damaged. To overcome this problem, one embodiment of the disclosed technology groups the ultrasound transducer elements into a multielement array in order to spread the stresses created by any single transducer over a larger area, or offsetting the stresses from the normal vibrational modes of the transducer element. FIGS. 6A and 68 illustrate one embodiment of a transducer array for applying acoustic energy to corresponding wells in a microplate. In the embodiment shown, an array comprises a sheet of piezoelectric material 250 having a first side 252 and a second side 254. The first side 252 is coated with a conductive material such as silver over its entire surface. The second side 254 includes two or more transducer patterns 256 and 258. The transducer patterns can be made via a number of techniques such as etching. In one embodiment, the transducer patterns 256, 258 are created with a photolithographic process by coating the side 254 with a conductive material followed by a resist material. The resist material is exposed with a mask pattern and then chemically etched to remove the conductive material where it is not desired. After etching the conductive material, the patterns of the transducers 256 and 258 are left on the surface of the piezoelectric sheet. In the embodiment shown, the transducers 256 and 258 are circular in shape to correspond to the shape of the bottom surface of the wells of the microplate. However, it would be appreciated that other shapes could be used if desired, or even no patterning at all.

In one embodiment, the conductive coating on the first side 252 of the substrate is connected via one or more electrical leads to one electrical potential such as ground, while the transducers 256, 258 are connected via individual leads to a positive potential. Upon the application of sufficient voltage signals to the transducers 256, 258, the transducers will produce ultrasonic sound waves that can be coupled into the individual wells of the microplate. The electrodes can be wired such that each transducer element is driven in parallel with other transducer elements or in a manner such that each individual transducer element can be driven separately from other elements.

Figure 7:
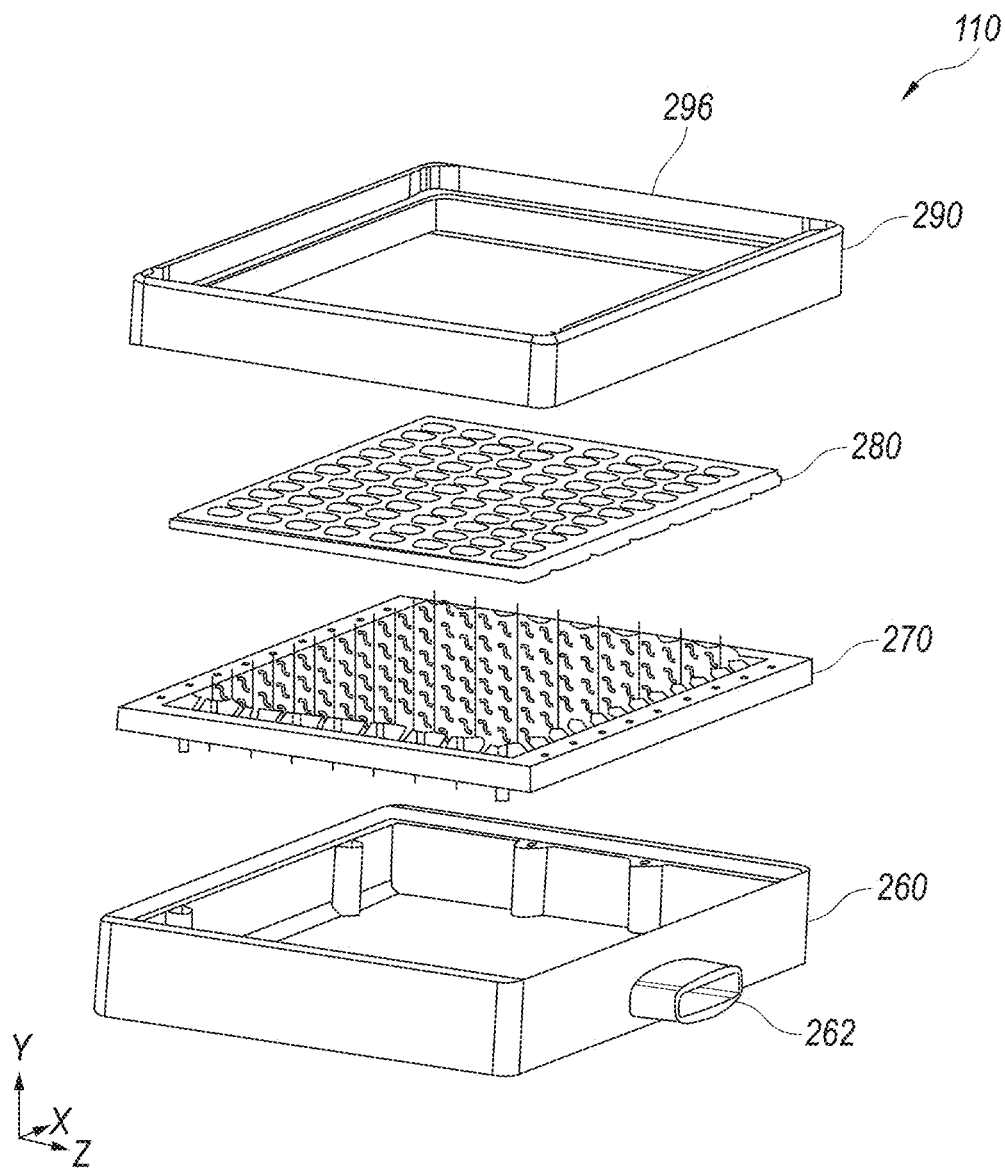
FIG. 7 shows an exploded view of a number of ultrasound transducers and a lens plate in a transducer assembly.

FIG. 7 is an exploded view of a transducer assembly 110 without the top cover that is constructed in accordance with one possible embodiment of the disclosed technology. The transducer assembly 110 includes a base 260, an electrode support plate 270, a plate 280 having transducers bonded to a bottom surface thereof and a top cap 290. The base 260 is a generally rectangular enclosure a closed bottom surface, and an opening 262 in a sidewall through which conductors to the individual transducer elements can be routed. The support plate 270 is constructed to support a number of spring loaded contacts or "pogo pins" in an array that corresponds to the arrangement of the transducer elements. In one embodiment, the contacts are wired in parallel so that individual wires do not need to be routed from each individual transducer element to a position outside the assembly. However, it is possible to wire each individual transducer element separately if desired, which may or may not include pogo pins.

Above the support plate 270 is the plate 280 with the one or more arrays of transducer elements secured to a bottom surface thereof with an acoustically matched epoxy or other adhesive. As will be explained in further detail below, in one embodiment the plate 280 includes a number of lenses positioned over a corresponding transducer element in order to focus ultrasound energy created by the transducer element towards a well of a microplate. In one embodiment, the plate 280 is made of a metal such as aluminum having the lenses formed directly into the plate 280. However, other materials such as ceramics could be used if desired. In yet another embodiment, separate lens elements may be secured to the plate 280. The top cap 290 fits over the surface of the plate 280 and is secured to the base plate 260 with screws or the like in order to secure the plate 280 and transducers against the number of spring loaded pins that are held in the support plate 270. A rim 296 extending around an inner perimeter of the top cap 290 supports a microplate (not shown) at a fixed distance from the top surface of the plate 280 so that ultrasound is focused at the correct location towards the wells of the microplate. In one embodiment, liquid, gel or other material is placed into an opening of the cap 290 prior to the placement of a microplate in order to effectively couple the acoustic energy produced by the transducers into the wells of the microplate.

Figure 8A:
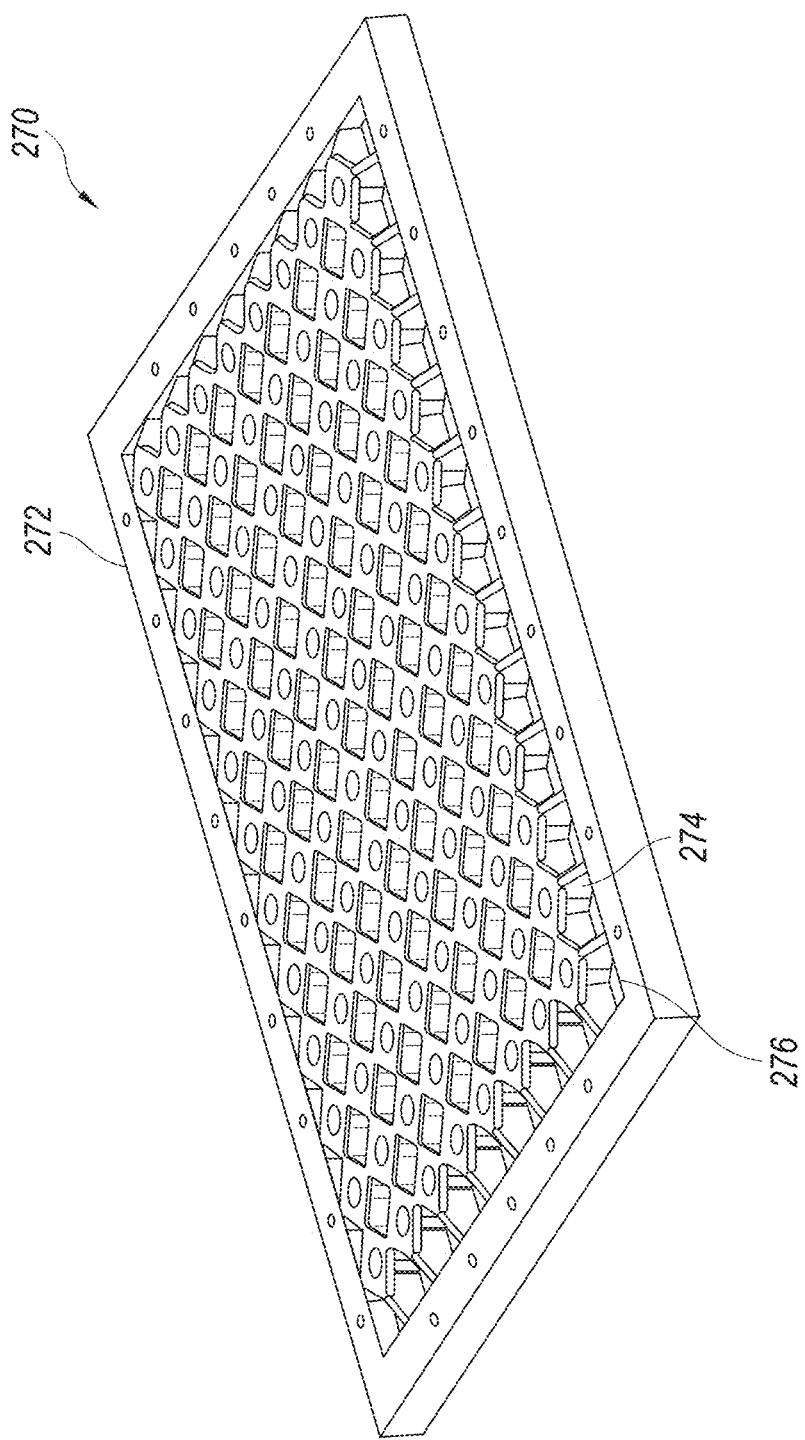
FIGS. 8A-8C show one method of making electrical connections to the transducers in a transducer assembly in accordance with an embodiment of the disclosed technology.

FIG. 8A shows one embodiment of the support plate 270 that supports a number of electrical contacts that connect to the various transducer elements of the transducer assembly. The support plate 270 has an outer rim 272 that surrounds an arrangement of cylindrical bores 274 in which individual contact pins are fitted. In one embodiment, the cylindrical bores 274 are supported by a honeycomb arrangement of fins 276 that extend outwardly from each of the bores. Spaces between the fins 276 serve to decrease the weight of the support plate 270. In the embodiment shown, the top surface of each cylindrical bore has a flat top section that is joined at its corners to an adjacent flat top section of another cylindrical bore. The pattern of cylindrical bores 274 is designed to match the corresponding pattern of transducer elements and also to the pattern of wells in the microplate. The support plate 270 can be molded, created by a 3-D printer or constructed using other techniques.

Figure 8B:
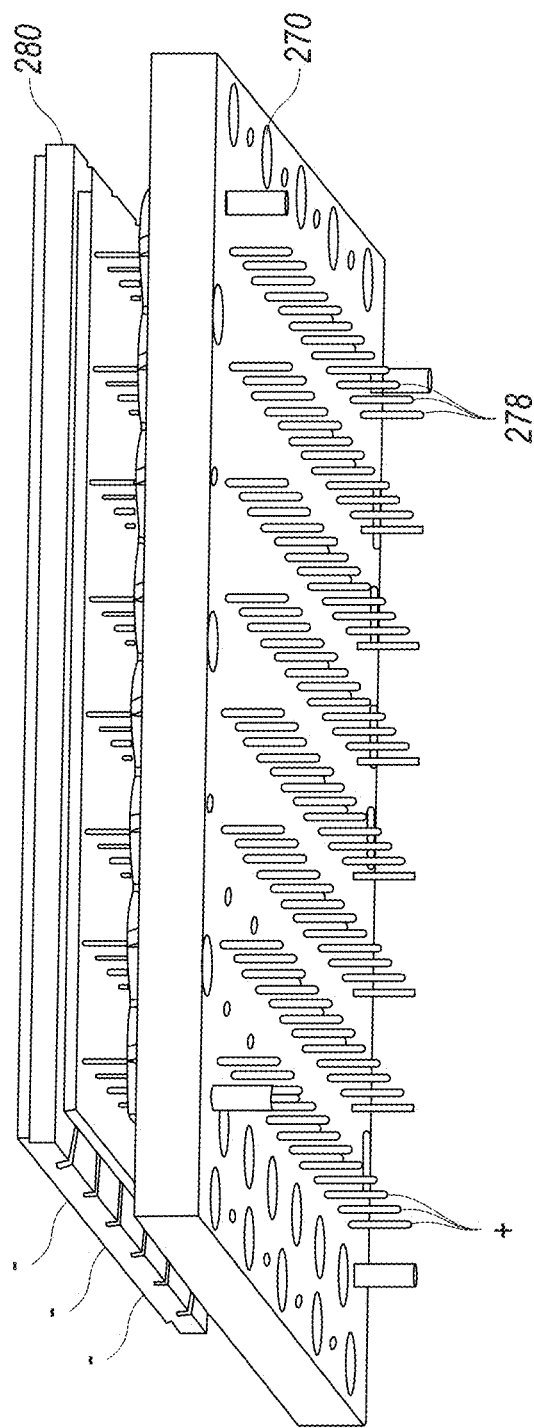
Figure 8C:
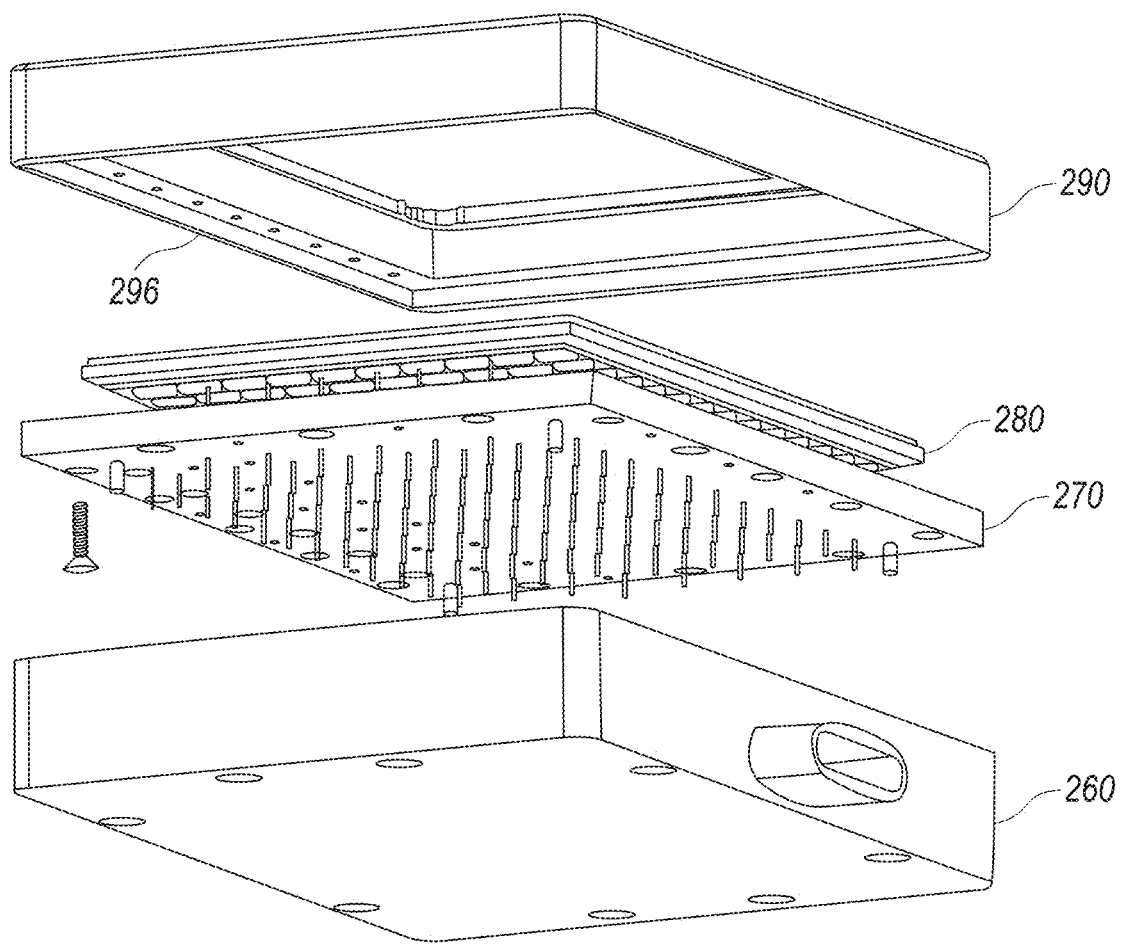

FIG. 8B illustrates how the conductive pins 278 are secured within the support plate 270 and engaged against the surface of the corresponding transducer elements that are on the bottom surface of the plate 280. The conductive pins can be press fit into a cylindrical bore or can be secured by an adhesive. Alignment pins at the corners of the support plate 270 align the plate when it is placed in the base section and also provide a vertical space for the pins. As shown in FIG. 8C, the support plate 270 is secured to the cap 290 of the ultrasound assembly with fasteners such as screws or the like. The top cap 290 is secured to the base 260 to complete the transducer unit.

Figure 9:
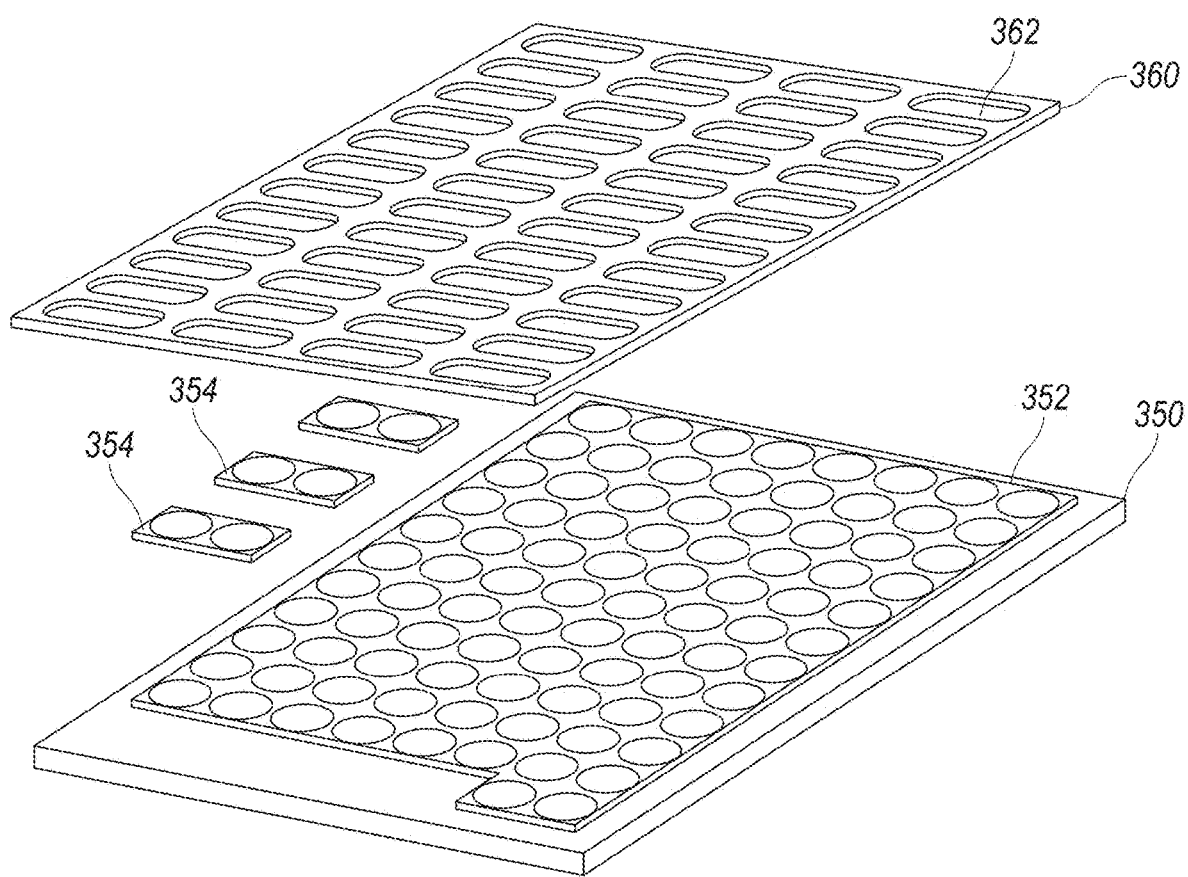
FIG. 9 illustrates how a circuit board can be used to make connections to the transducer elements in accordance with an embodiment of the disclosed technology.

As an alternative to using spring-loaded conductors, other mechanisms can be used to supply the required current and voltages to the transducer elements. FIG. 9 illustrates one embodiment that uses a printed circuit board to supply driving signals to the transducer elements. In this embodiment, a lens plate 350 has a number of transducer elements 352 secured to a rear surface thereof. In the embodiment shown, each of the transducer elements is formed as an array 354 of two transducer elements on a section of piezoelectric substrate. Groups of these transducer element pairs are arranged in a pattern corresponding to the pattern of wells in a corresponding microplate. In this embodiment, a printed circuit board 360 has a number of openings 362 that correspond to the position of the transducer elements. The dimensions of the openings 362 are slightly smaller than the dimensions of the transducer elements so that a portion of the printed circuit board 360 overlaps a portion of the outer perimeter of the transducer elements. Therefore, electrical contacts placed on the surface of the printed circuit board that engages the outer portion of the transducer elements can be used to deliver signals to the transducer element. Traces can be routed through the printed circuit board in order to wire the transducer elements in parallel, in groups of transducer elements or individually. It is recognized that the pins or printed circuit board are only to deliver electrical signals to the transducer elements. Direct soldering and other methods exist to deliver electrical signals.

Figure 10:
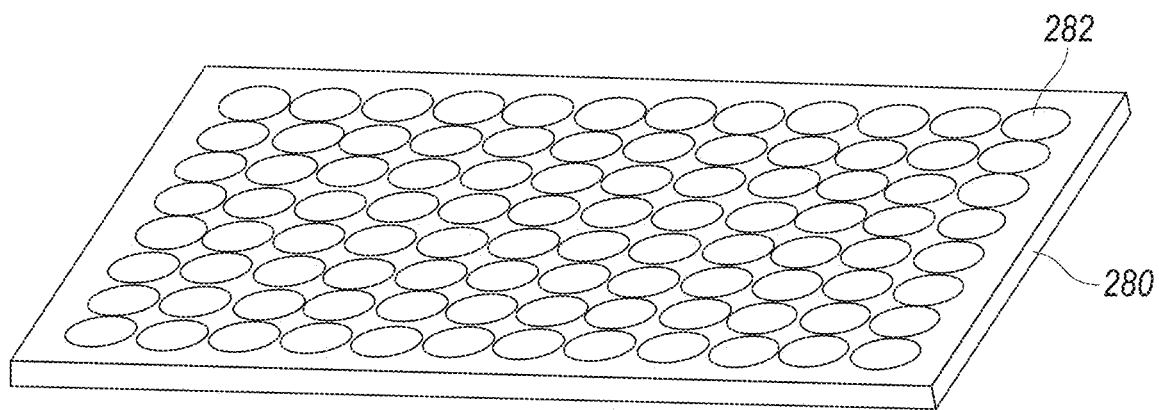
FIG. 10 shows one example of a lens plate in accordance with an embodiment of the disclosed technology.

FIG. 10 illustrates further details of the plate 280 in accordance with the embodiment of the disclosed technology. As indicated above, the plate can be made of a metal such as aluminum, ceramic or graphite or other materials having good acoustic transmission characteristics that couple the acoustic energy produced by the transducers into the wells of a corresponding microplate. In the embodiment shown, the top surface of the plate 280 includes a number of concave lenses 282 formed therein. In one embodiment, each lens is constructed to focus ultrasound energy from a transducer element at a distance corresponding to the diameter of the lens (i.e. an F1 lens). However, it will be appreciated that other lens designs could be used. The lens plate can be cast or machined.

Figure 11:
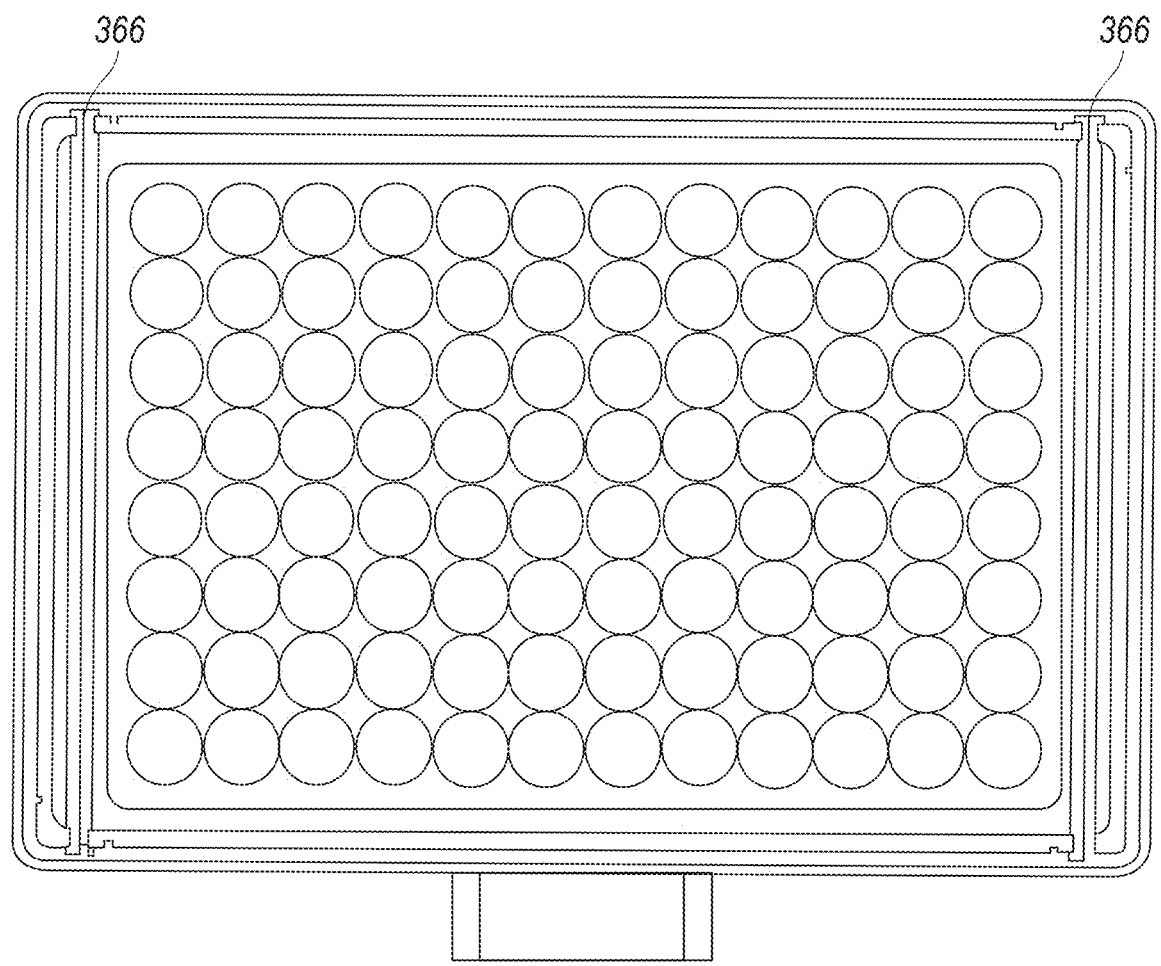
FIG. 11 shows a transducer assembly with spacers that allows for the adjustment in height between different microplates and the transducers/lenses in accordance with an embodiment of the disclosed technology.

FIG. 11 illustrates one embodiment of a system for securing a microplate at a desired level above the lens plate. In one embodiment, the transducer assembly includes a number of adjustable spacers 366 having a height selected to position the bottom of the microplate wells at a desired height above the surface of the lenses. Different spacers can be selected depending upon the type of microplate being used in order to ensure that the focal zone of the transducers is positioned in a desired portion of the wells. In one embodiment, the spacers 366 are rods having a diameter selected in accordance with the type of microplate being used. The rods are positioned at opposite ends of the lens plate. The microplate is spaced from the lens plate by a distance corresponding to the diameter of the rods set to the height above the lenses.

Figure 12B:
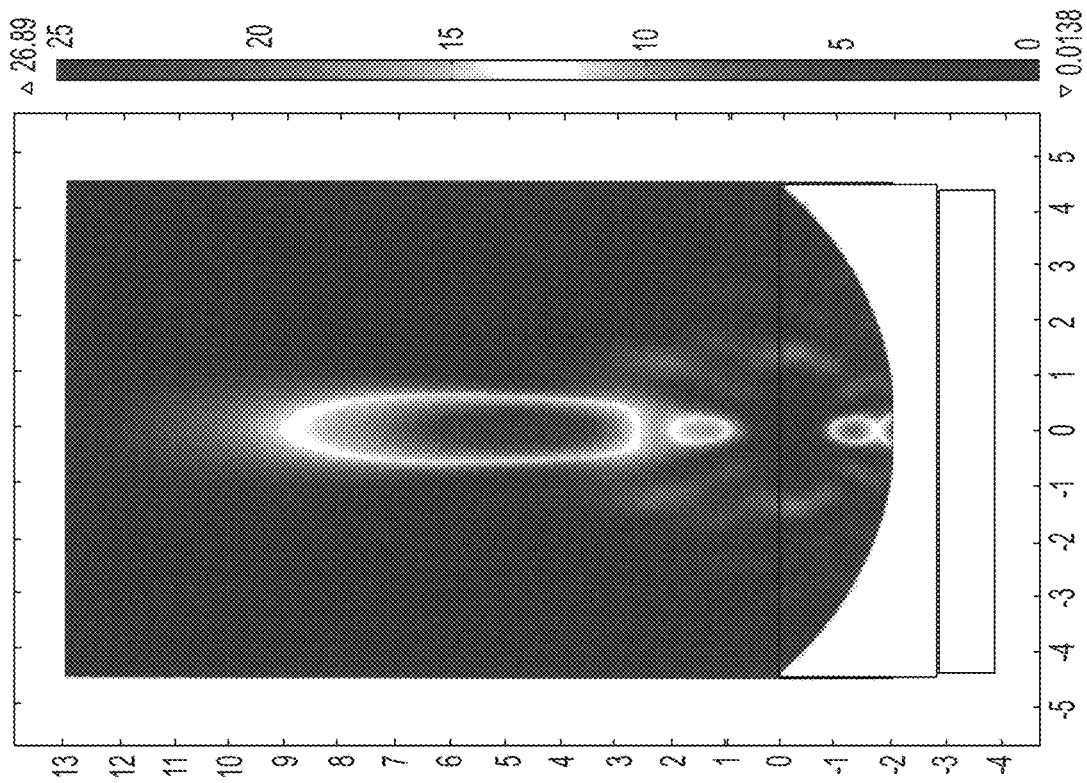
FIGS. 12A and 12B illustrate measured pressures in a water tank, and a model of the focal zone caused by a transducer element, superimposed with a well in accordance with an embodiment of the disclosed technology.
Figure 12A:
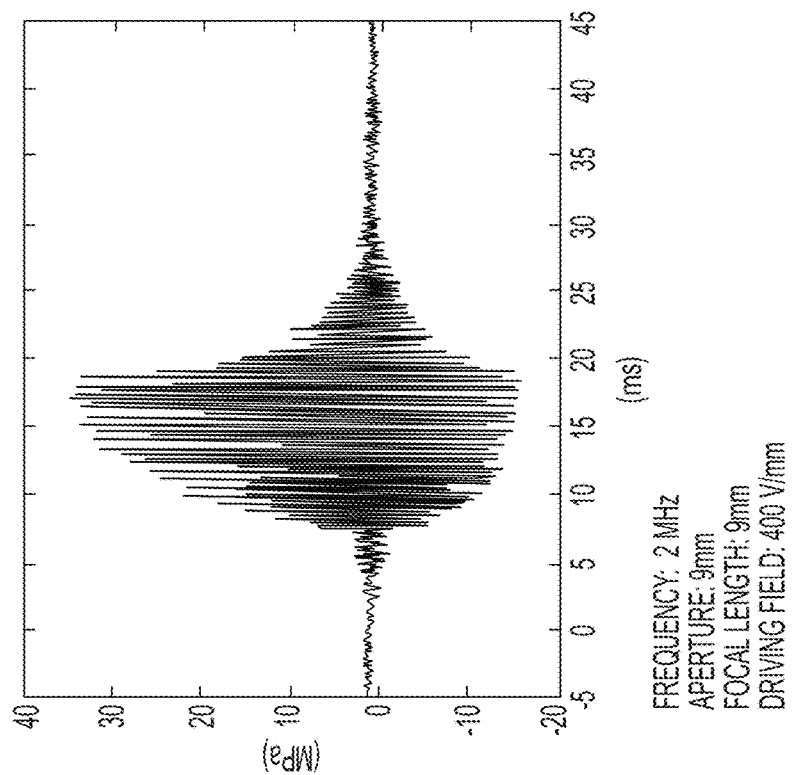

FIGS. 12A and 12B illustrate the acoustic pressures generated by a single transducer element. FIG. 12A shows the measured acoustic pressure in a water tank at the focus of the transducer element. A 15 microsecond driving pulse at a frequency of 2 MHz and a driving field of 400 Volts/mm creates a positive pressure in excess of 30 MPa and a negative pressure of over 15 MPa in approximately 10 microseconds. The pressures rise and fall as the driving signal is applied to the transducer element and is then turned off. FIG. 12B shows a mathematical simulation of the pressures in a microplate well. As can be seen, the area of greatest absolute pressure is created at a distance 4-7 mm above the bottom surface of the well and in the center of the well. Pressures in this range have been determined to have sufficient power to create inertial cavitation in a biological sample. The lower limit of pressures required to induce or facilitate inertial cavitation has not been determined and may be lower than the pressures described. As an example, it has been determined that negative pressures should be greater than 5 MPa. In practice, the voltages applied to the transducer elements are increased until cavitation can be detected. The focus can be adjusted to accommodate more or less sample in the well by changing one or more of the lens geometry, the frequency of the ultrasound signals applied or the spacing between the transducer elements and microplate. As previously stated, one does not have to have the focus inside the well. Cavitation can also be generated in the pre-focal or post-focal region.

Figure 13A:
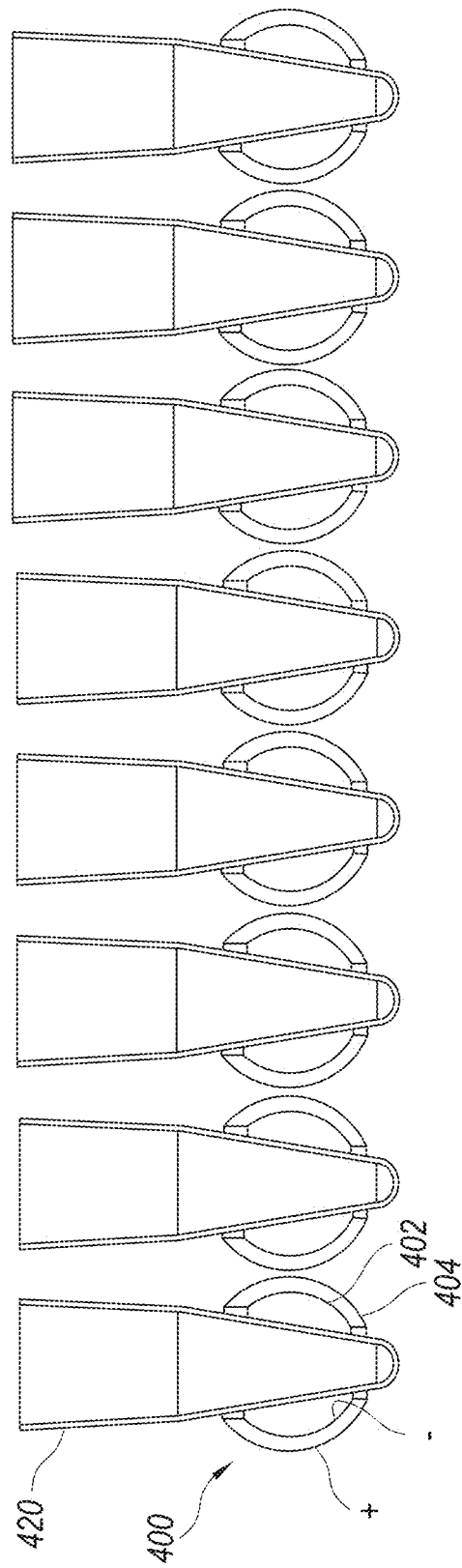
FIG. 13A shows a number of spherical transducers that accept conical wells of a microplate in accordance with an embodiment of the disclosed technology.
Figure 13B:
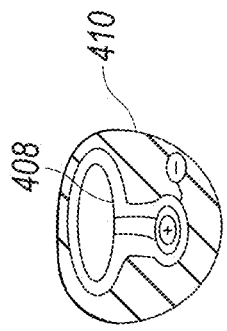
FIG. 13B shows a wraparound electrode that can be used with the transducers shown in FIG. 13A.

In some instances, the wells of the microplate may not be cylindrical. Therefore, embodiments of the disclosed technology are constructed and arranged to receive non-cylindrical wells in order to focus the ultrasound energy into the biological samples held by the wells. In an embodiment shown in FIG. 13A, a number of transducer elements 400 are generally spherical having a hole at their top and bottom that receive a conical well 420 of a microplate. The transducer elements 400 have an inner surface 402 and an outer surface 404. The inner surface 402 includes a first electrode thereon and the outer surface 404 includes a second electrode thereon. In one embodiment, a wire can be bonded to the inner surface 402 and routed through a hole in the transducer element to a signal source. In another embodiment as shown in FIG. 13B, a wraparound electrode 408 is electrically connected to the electrode on the inner surface and terminates on the exterior surface of the spherical transducer. An outer electrode 410 on the outer surface of the transducer element surrounds but does not touch the electrode 408. In one embodiment, the electrodes 408 and 410 are connected by wires to a signal source to cause the spherical transducer element 400 to vibrate and produce ultrasound energy.

In one embodiment, a coupling material such as liquid or a gel is disposed between the interior surface of the transducer element 400 and a conical well 420 of a microplate. The spherical shape of the transducer elements 400 cause the acoustic energy created by the application of a positive and negative voltage of the interior and exterior electrodes of the spherical transducer elements to be focused within the conical well of the microplate element. In one embodiment, the spherical transducer elements are cast as hemispheres and are sintered together once the electrodes are patterned on the inside and outside surfaces of the electrode elements.

Figure 14:
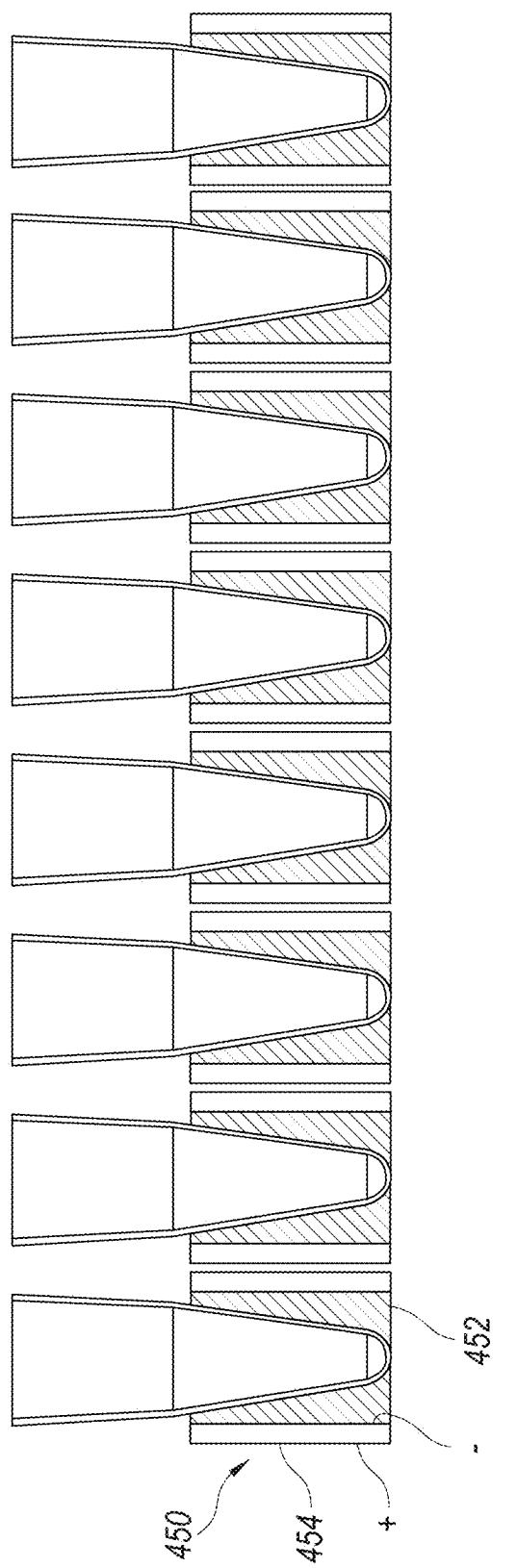
FIG. 14 shows a number of cylindrical transducers that accept conical wells of a microplate in accordance with an embodiment of the disclosed technology.

FIG. 14 illustrates yet another alternative embodiment of a number of transducer elements that are designed to transmit ultrasound energy into a noncylindrical well of a microplate. In this embodiment, a number of transducers 450 are generally cylindrical with an inner diameter that is large enough to accept a portion of a conical well of a microplate. The transducer elements include an inner surface 452 and an outer surface 454. Electrodes placed on the inner and outer surfaces allow the application of a voltage and current signal to the transducer element to cause it to vibrate and produce ultrasound energy which is focused in a zone within the well of the microplate. In one embodiment, a coupling fluid is placed between the inner surface of the transducer 450 and the exterior surface of the microplate wells to couple the acoustic energy into the microplate well. In one embodiment, wires can be used to connect the electrodes on the interior surface 452 and the outer surface 454 to a signal source. In an alternative embodiment, wrap around electrodes can be used to route an electrode that is electrically coupled to the electrode on the interior surface 452 to a position that is on the exterior of the cylindrical transducer 450. Wires or other conductors can then be used to connect the electrodes to a current and voltage source.

Figure 15:
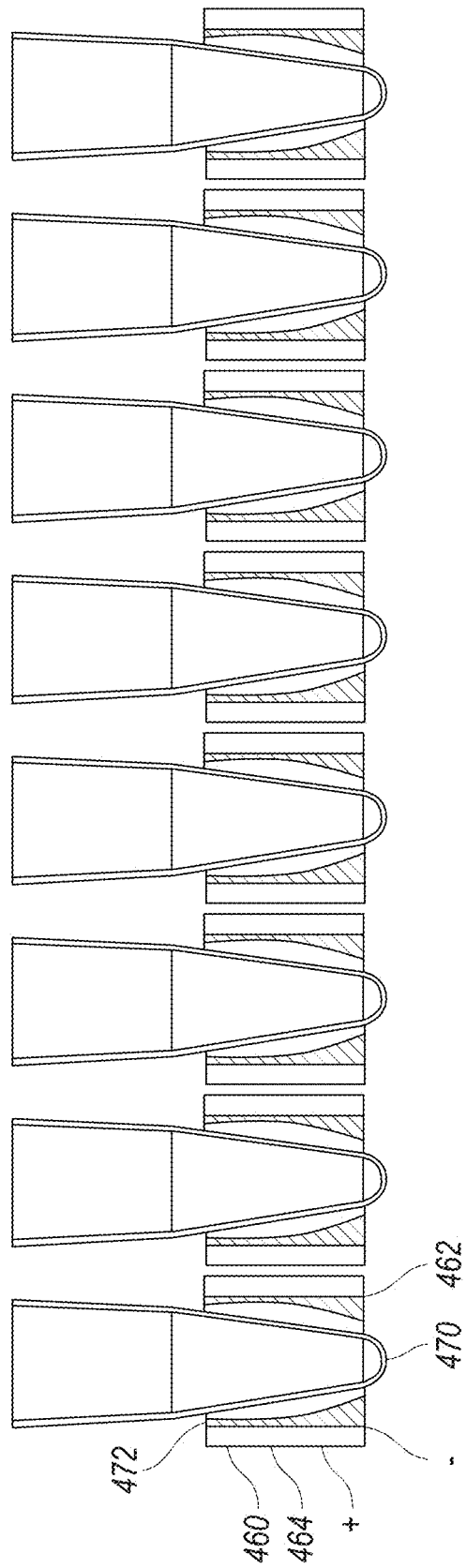
FIG. 15 shows a number of cylindrical transducers with built in lenses that accept conical wells of a microplate in accordance with an embodiment of the disclosed technology.

FIG. 15 illustrates a number of transducer elements in accordance with another embodiment of the disclosed technology. Each of these transducer elements is designed to focus ultrasound energy into a non-cylindrical well of a microplate. In this example, each transducer 460 has a generally cylindrical shape with an inner diameter that is sized to receive a portion of the conical well of a microplate. An electrode 462 on an interior surface of the transducer element and an electrode 464 on the exterior surface of the transducer element are used to supply a current and voltage to the transducer element. In this embodiment, a lens 470 is positioned between the interior surface of the transducer element and the well of the microplate. In the embodiment shown, the lens 470 has a radial thickness that varies parabolically whereby it is thinner at a top end 472 of the transducer element and radially thicker at a bottom surface 474 of the transducer element. In one embodiment, the lens 470 is made of an acoustically transparent material such as aluminum or a ceramic. The design of the lens is selected to focus ultrasound energy created by the cylindrical electrode into the middle of the well.

Figure 16:
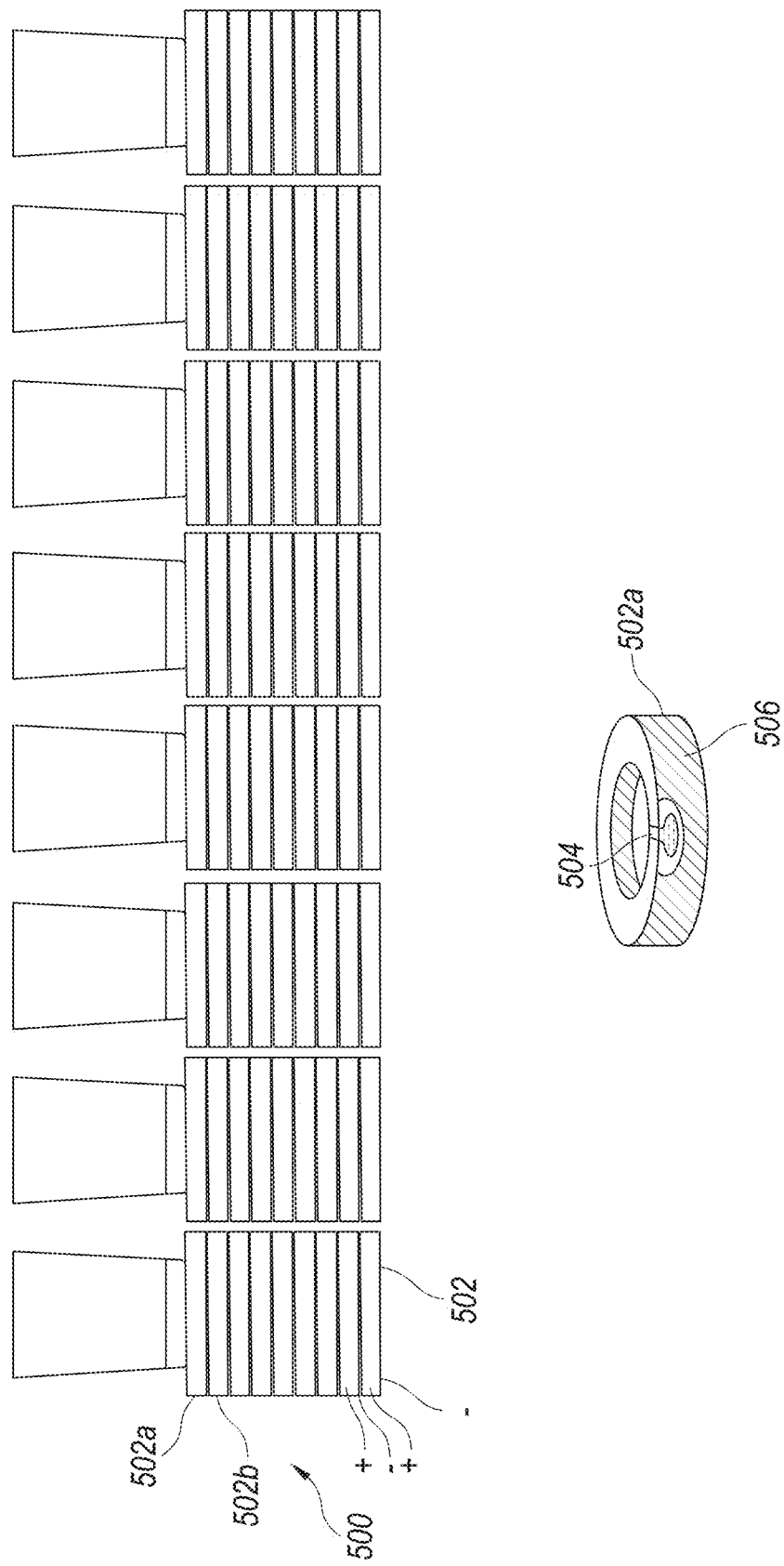
FIG. 16 shows a number of annular transducers that form a phased array and accept conical wells of a microplate in accordance with an embodiment of the disclosed technology.

Yet another alternative embodiment of a transducer element in accordance with the disclosed technology is shown in FIG. 16. In this embodiment, a transducer 500 includes a number of annular transducer elements 502a, 502b . . . 502i. Each of the transducer elements 502a-502i is annular in shape with an outer electrode 506 disposed on the outer perimeter of the transducer element and an inner electrode 504 on an inner perimeter of the transducer. Again, as described above, connections to the electrodes can be made with wires or a wraparound electrode can be used to electrically connect to the inner electrode. Application of a current and voltage signal to the inner and outer electrodes cause the transducer elements 502a-502i to produce ultrasound signals. Because the elements 502a-502i are stacked, they can be driven as a phased array to control focusing of the ultrasound waves into a desired portion of the wells of a microplate.

Figure 17:
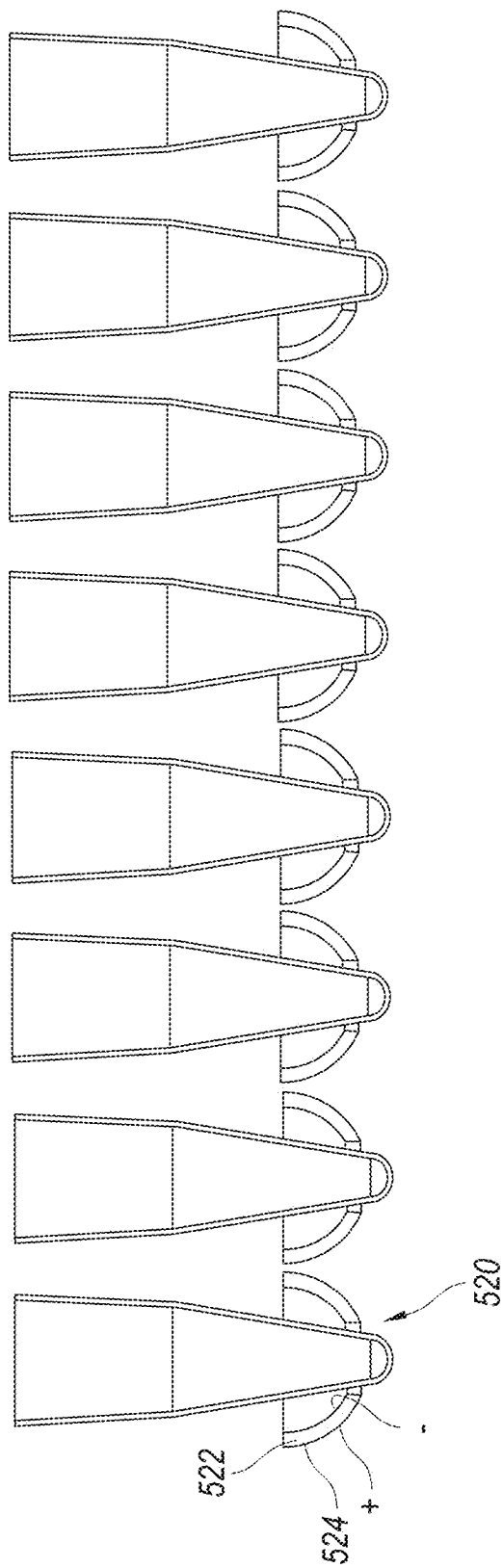
FIG. 17 shows a number of semi-spherical transducers that accept conical wells of a microplate in accordance with an embodiment of the disclosed technology.

FIG. 17 shows yet another embodiment of a transducer designed to direct ultrasound energy into the non-cylindrical wells of a microplate. In this embodiment, each transducer 520 comprises a hemispherical shell having an inner surface 522 and an outer surface 524. The shell is arranged as a cup whereby the open portion of the hemisphere faces toward the top of the well. The transducer elements have electrodes on the inner and outer surfaces of the hemisphere such that application of a current and voltage signal to the inner and outer electrodes causes the transducer element 520 to produce ultrasound energy and direct it into a desired zone within the conical portion of the microplate well. Because the transducer elements are partially spherical, ultrasound energy is generally directed towards the geometric center of the hemisphere. The transducer element includes a hole through its lower surface through which a tip of the microplate well extends. In one embodiment, separate wires can be attached to the inner and outer electrodes of the transducer element 520. Alternatively, wrap-around electrodes can be used to allow the wires that connect to both electrodes to be located on the exterior surface of the electrode.

Figure 18:
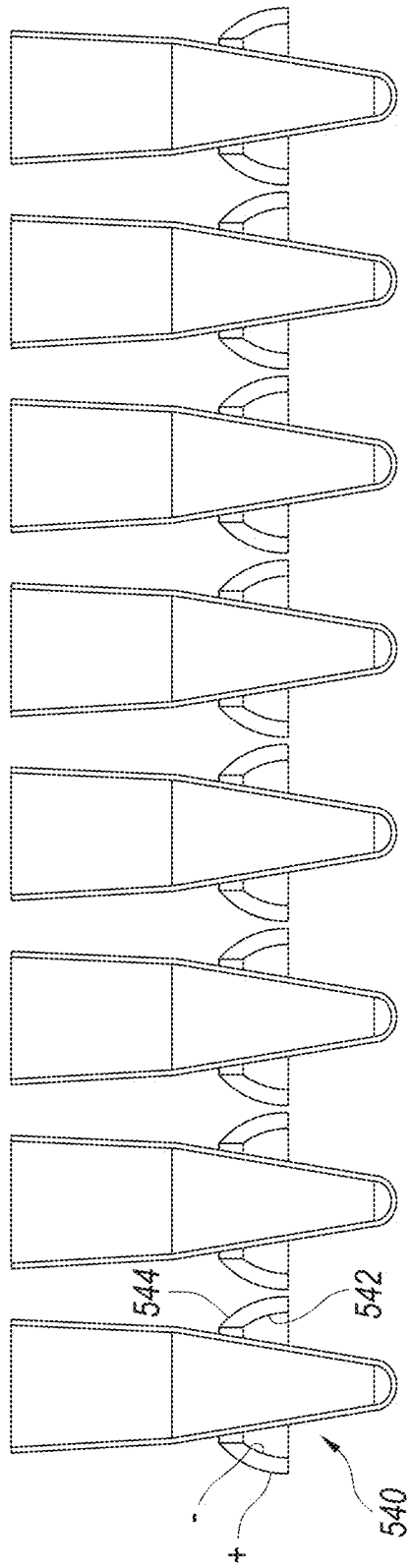
FIG. 18 shows a number of semi-spherical transducers that accept conical wells of a microplate in accordance with one embodiment of the disclosed technology.

FIG. 18 illustrates a number of transducer elements that are designed to direct ultrasound energy into a non-cylindrical well of a microplate in accordance with an embodiment of the disclosed technology. In this embodiment, the transducer elements 540 are hemispherically shaped with an interior surface 542 and an exterior surface 544. Electrodes are placed on the interior and outer surfaces such that application of a current and voltage signal to the electrodes causes the transducer element 540 to produce ultrasonic energy which is focused at a desired location in the well of the microplate. In this embodiment, the transducer elements are arranged as umbrellas whereby the larger diameter of the hemisphere is pointed towards the bottom of the microplate well. Again, because the transducer element 540 is hemispherically shaped, the ultrasound energy produced will be focused at roughly the geometric center of the transducer. A hole positioned at the top surface of the electrode receives the tip of the microplate well such that the microplate well extends through the center of the transducer element 540. Connections to the electrodes on an interior of the transducer elements can be made with individual wires. Alternatively, a wraparound electrode can be used to allow connections to be made on the outside of the transducer element.

Figure 19:
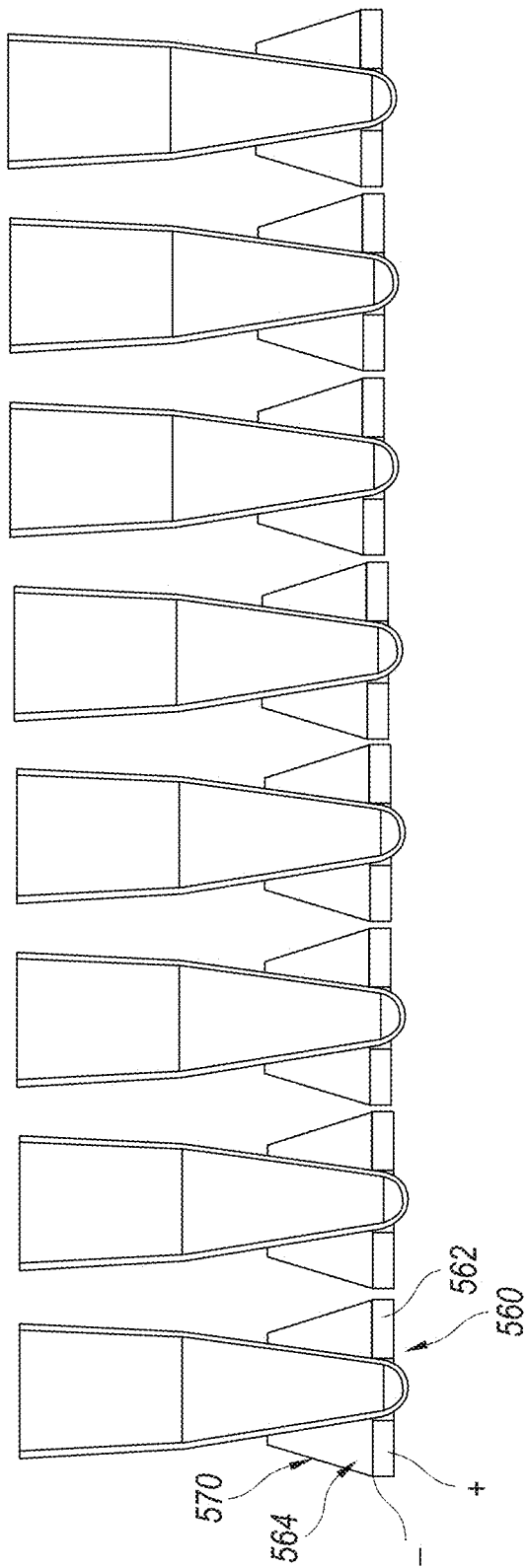
FIG. 19 shows a number of annular transducers with waveguides on one surface that accept conical wells of a microplate in accordance with an embodiment of the disclosed technology.

FIG. 19 illustrates yet another alternative embodiment of a transducer. In this embodiment, a transducer 560 is formed as a generally flat disk with a circular perimeter and a hole in the center. A first electrode is formed on the bottom surface 562 of the disk and a second electrode is formed on the top surface 564 of the disk. The tip of the conical well of the microplate extends through a hole at the center of the disk. Above the top surface of the transducer element 560 is an acoustic reflector 570. The acoustic reflector has a lower surface that engages the top surface 564. The diameter of the acoustic reflector tapers from a diameter equal to the diameter of the disk and gets smaller as it extends upwards away from the top surface 564 of the transducer 560 until it has a lesser diameter, thereby giving the acoustic reflector 570 a generally bell shape. The acoustic reflector 570 operates as an acoustic waveguide to focus the ultrasound energy produced by the transducer element 560 at a desired location in the well of the microplate. Suitable materials for the acoustic reflector 570 include metals, such as aluminum, or ceramics.

Figure 20:
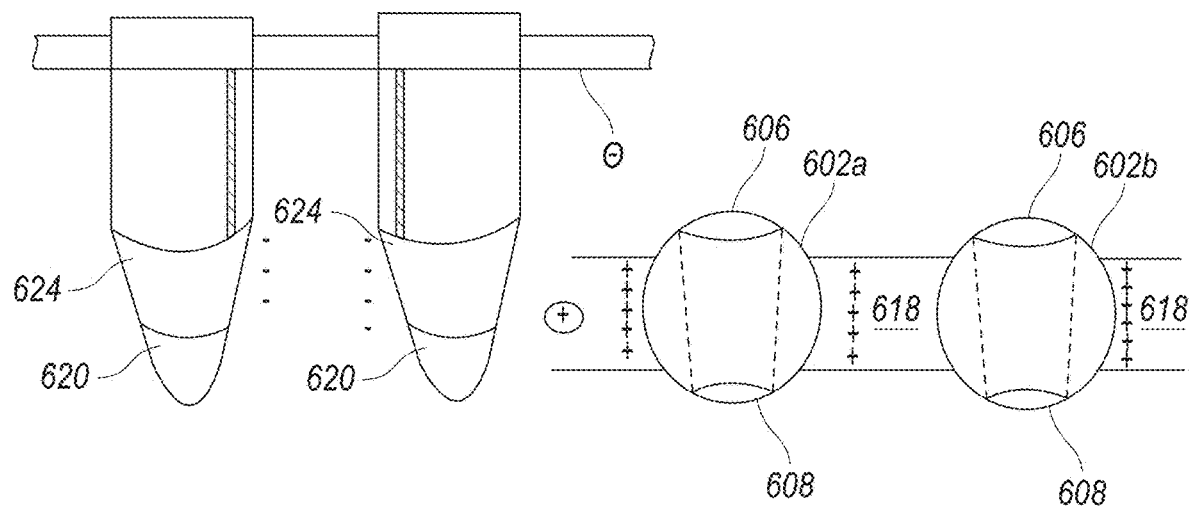
FIG. 20 shows a number of spherical transducers that accept conical wells of a microplate in accordance with one embodiment of the disclosed technology.

In yet another alternative embodiment of the disclosed technology, the transducer elements can be capacitively coupled to the well of the microplate. FIG. 20 illustrates an example where a pair of transducer elements 602a and 602b are generally spherical in shape with a top hole 606 on its top surface and a smaller hole 608 on its bottom surface. Dimensions of the holes 606 and 608 are designed to accept a correspondingly conical shaped well 620 of a microplate. In this embodiment, the outer portions of the transducers 602a, 602b are seated in a conductive material such as a conductive epoxy that forms an electrode on the exterior surface of the transducer elements. The second electrode is formed on the exterior surface of the microplate wells. As shown, an electrode 624 is disposed on the outer conical portion of a microplate well. The holes through the transducers are tapered such that insertion of the conical well into the holes of the transducer elements causes the electrode 624 to be positioned against an interior surface of the transducer element. Application of a suitable current and voltage signal between the conductive material 618 and the corresponding electrodes 624 on the outer surface of the well causes the transducer elements 602a, 602b to produce ultrasound energy which is focused at a location in the interior of the microplate wells. In another embodiment, there may be a gap between the electrode on the microplate well and the interior of the transducer element (e.g. a spherical transducer element).

Figure 21:
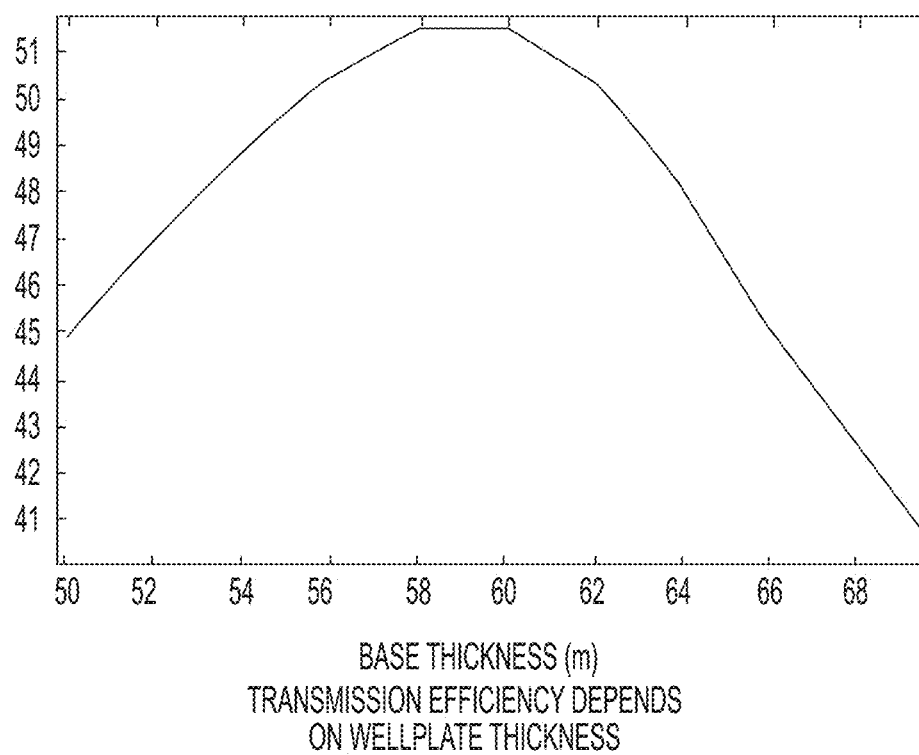
FIG. 21 is a graph of the expected transmission efficiency for ultrasound into a flat bottomed well of a microplate as a function of the base thickness of the bottom of the well.

In some embodiments, it has been determined that the thickness of the bottom portion of the well of a microplate affects the transmission of acoustic energy into the well. The efficiency has been determined to increase to a maximum efficiency at some point between a minimum and maximum thickness of the well bottom. In one embodiment shown in FIG. 21, it has been calculated that the efficiency rises as the thickness is increased from 52 microns to a maximum efficiency occurring at approximately 59 microns and then decreases as the thickness increases from 59 microns to 68 microns. The exact values depends on the material properties of the microplate. Therefore, it can be seen that the thickness of the base of the microplate well can be selected in order to achieve maximum transmission efficiency. In one embodiment, the base thickness is selected to be approximately 59 microns in order to achieve maximum transmission of acoustic energy into the well.

Figure 22:
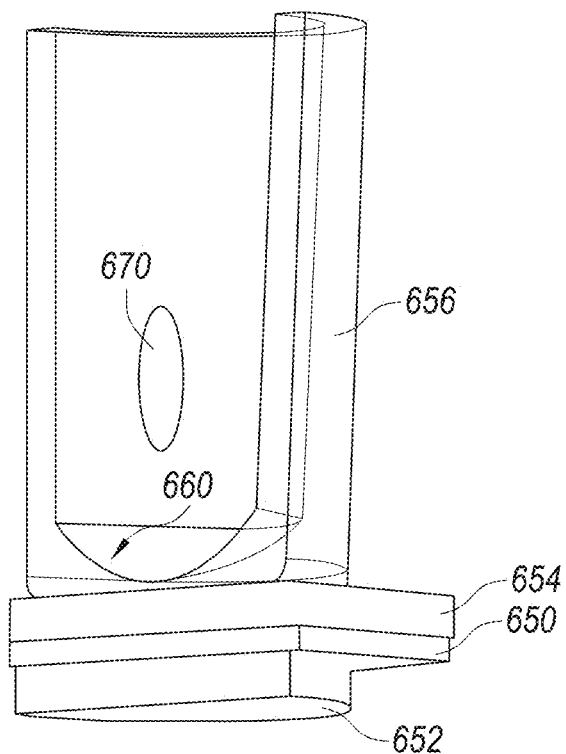
FIG. 22 illustrates a microplate well having an integrated lens to focus ultrasound energy from a transducer into an interior portion of the well in accordance with an embodiment of the disclosed technology.

In yet an alternative embodiment, the bottom of the microplate well can be molded as a lens to focus ultrasound energy into the well, and as such may not require a separate focusing lens between the transducer and the bottom of the microplate. FIG. 22 shows a cutaway view of a microplate well 656 having a lens 660 integrally formed therein. In the example shown, a sheet of piezoelectric material 650 has a transducer element 652 formed onto a bottom surface. The transducer element 652 has a generally circular shape that matches the diameter of the cylindrical microplate well 656. A coupling material such as water or gel 654 is positioned between the bottom of the well 656 and the attachment plate for the transducer, 650. The attachment plate 650 may be metal and used to remove heat from the water or gel pad. In this embodiment, the bottom 661 and/or sidewalls of the well of the microplate well are not of a uniform thickness but have a thickness that varies to focus acoustic energy from the transducer element 652 towards an interior portion of the well 656. In one embodiment, the bottom of the well has a concave shape to act as a lens that focuses ultrasound energy into an interior portion of the well. The well 656 can be injection-molded to form the lens 660 in its desired shape and focus the ultrasound energy into the desired portion of the well. Biological materials within the well 656 are sheared due to the inertial cavitation occurring in the focal zone 670. After application of the ultrasound energy to the wells of the microplate, the samples are ready for further processing.

From the foregoing, it will be appreciated that specific embodiments of the invention have been described herein for purposes of illustration, but that various modifications may be made without deviating from the scope of the invention. For example, although the disclosed embodiments show the use of a single transducer element positioned to direct ultrasound into a single sample well, it will be appreciated that two or more transducer elements could be positioned to direct ultrasound into a single well. Furthermore, although the samples are described as being held in the wells of a microplate, it will be appreciated that the size of the system can be adjusted to direct ultrasound into other sample holders (e.g. an array of petri dishes etc.) In yet another embodiment, the transducer elements are formed from a sheet of piezoelectric material with a conductor one side and a flex circuit joined to the other side, where the flex circuit includes conductors that form the transducers when secured to a piezoelectric material. Alternatively, the array of transducers can be made by grouping individual transducer elements and securing them via an adhesive or the like to a common support structure (e.g. a piece of aluminum) such that the support structure absorbs a portion of the stresses created from each of the transducers secured thereto. Accordingly, the invention is not limited except as by the appended claims.

We claim:

1. A system for shearing biological materials, the system comprising:
   a microplate comprising wells configured to hold biological samples, bottom walls of the wells having curved concave inner surfaces and curved concave outer surfaces;
   a transducer array disposed underneath the microplate and comprising transducer elements configured to emit ultrasound in an upward direction toward the bottom walls of the wells of the microplate;
   a lens plate affixed to the transducer array and disposed between the microplate and the transducer array, the lens plate comprising concave lenses respectively disposed between the bottom walls of the wells and the transducer elements; and
   a coupling material disposed between the lens plate and the wells, the coupling material being in direct contact with the concave lenses and the curved concave outer surfaces of the bottom walls of the wells.

2. The system of claim 1, wherein thicknesses of the bottom walls of the wells along the upward direction are between 52 microns and 68 microns.

3. The system of claim 1, further comprising:
a signal generator configured to output a driving signal comprising pulses with durations of 15 microseconds; and
an amplifier configured to:
generate an amplified signal by increasing a power of the driving signal; and
cause the transducer elements to output the ultrasound at a frequency of 2 megahertz (MHz) by outputting the amplified signal to the transducer elements.

4. The system of claim 1, wherein foci of the concave lenses are disposed inside of the wells.

5. A system comprising:
a well configured to hold a biological sample, the well comprising a wall having at least one curved surface;
a transducer element pointed toward the wall and configured to emit ultrasound, a focus of the ultrasound being disposed inside of the well; and
a concave lens disposed between the wall and the transducer element.

6. The system of claim 5, wherein the ultrasound induces inertial cavitation in the biological sample.

7. The system of claim 6, wherein the biological sample comprises at least one of chromatin, deoxyribonucleic acid (DNA), or a cell, and wherein the inertial cavitation shears the biological sample.

8. The system of claim 5, wherein a thickness of the wall of the well along a direction of the ultrasound is between 52 microns and 68 microns.

9. The system of claim 5, wherein a frequency of the ultrasound is 2 megahertz (MHz).

10. The system of claim 5, further comprising:
a signal generator configured to generate a driving signal comprising pulses with a duration of 15 microseconds; and
an amplifier electrically coupled between the signal generator and the transducer element, the amplifier being configured to generate an amplified signal by increasing a power of the driving signal.

11. The system of claim 5, wherein the focus of the ultrasound induces a negative pressure that is between 5 megapascals (MPa) and 30 MPa in the biological sample with respect to an atmospheric pressure.

12. The system of claim 5, further comprising:
a coupling material disposed between the well and the transducer element, the coupling material being in direct contact with the concave lens and the wall of the well.

13. The system of claim 1, wherein the concave lenses comprise at least one of aluminum, graphite, or a ceramic.

14. The system of claim 1, wherein the transducer elements comprise:
a sheet comprising a piezoelectric material;
a first conductive pattern disposed on a first side of the piezoelectric material, disposed between the piezoelectric material and the lens plate, and electrically coupled to ground;
second conductive patterns disposed on a second side of the piezoelectric material, the piezoelectric material being disposed between the first conductive pattern and the second conductive patterns, widths of the second conductive patterns being narrower than a width of the first conductive pattern; and
a signal generator electrically coupled to the second conductive patterns.

15. The system of claim 14, wherein the second conductive patterns comprise circular patterns corresponding to shapes of the wells.

16. The system of claim 5, wherein the transducer element comprises:
a piezoelectric material;
a first conductive pattern electrically coupled to ground, the first conductive pattern being disposed on a first surface of the piezoelectric material and between the piezoelectric material and the concave lens;
a second conductive pattern disposed on a second surface of the piezoelectric material, the piezoelectric material being disposed between the first conductive pattern and the second conductive pattern, a width of the second conductive pattern being narrower than a width of the first conductive pattern; and
a signal generator electrically coupled to the second conductive pattern.

* * * * *